US012774326B2

(12) United States Patent
Okazawa

(10) Patent No.: US 12,774,326 B2
(45) Date of Patent: Oct. 27, 2026

(54) AGENT FOR PREVENTING OR TREATING FRONTOTEMPORAL LOBAR DEGENERATION

(71) Applicant: NATIONAL UNIVERSITY CORPORATION TOKYO MEDICAL AND DENTAL UNIVERSITY, Tokyo (JP)

(72) Inventor: Hitoshi Okazawa, Tokyo (JP)

(73) Assignee: INSTITUTE OF SCIENCE TOKYO, Tokyo (JP)

( * ) Notice: Subject to any disclaimer, the term of this patent is extended or adjusted under 35 U.S.C. 154(b) by 635 days.

(21) Appl. No.: 18/256,222

(22) PCT Filed: Dec. 6, 2021

(86) PCT No.: PCT/JP2021/044619
§ 371 (c)(1),
(2) Date: Jun. 7, 2023

(87) PCT Pub. No.: WO2022/124247
PCT Pub. Date: Jun. 16, 2022

(65) Prior Publication Data

US 2024/0025985 A1 Jan. 25, 2024

(30) Foreign Application Priority Data

Dec. 9, 2020 (JP) ................................ 2020-204343

(51) Int. Cl.
*C07K 16/24* (2006.01)
*A61P 25/28* (2006.01)

(52) U.S. Cl.
CPC .............. *C07K 16/24* (2013.01); *A61P 25/28* (2018.01); *C07K 2317/21* (2013.01)

(58) Field of Classification Search
CPC ...................................................... C07K 16/24
USPC ...................................................... 424/142.1
See application file for complete search history.

(56) References Cited

U.S. PATENT DOCUMENTS 12,319,731 B2 * 6/2025 Okazawa ............... C07K 16/24

FOREIGN PATENT DOCUMENTS

| | | | |
|---|---|---|---|
| EP | 3764102 | A1 | 3/2019 |
| EP | 3854875 | A | 7/2021 |
| WO | 2019/172427 | A1 | 12/2019 |
| WO | 2020/059847 | A1 | 3/2020 |

OTHER PUBLICATIONS

Lundbäck et al (Hepatology, 2016, 64(5): 1699-1710).*
Boxer Adam L. et al: "New directions in clinical trials for frontotemporal lobar degeneration: Methods and outcome measures", Alzheimer's & Dementia, vol. 16, No. 1, Jan. 1, 2020 (Jan. 1, 2020), pp. 131-143.
Nilson Ashley N. et al: "Tau Oligomers Associate with Inflammation in the Brain and Retina of Tauopathy Mice and in Neurodegenerative Diseases", Journal of Alzheimer's Disease, vol. 55, No. 3, Dec. 6, 2016 (Dec. 6, 2016), pp. 1083-1099.
Nishibori Masahiro et al: "Anti-HMGB1 monoclonal antibody therapy for a wide range of CNS and PNS diseases", Journal of Pharmacological Sciences, vol. 140, No. 1, May 1, 2019 (May 1, 2019), pp. 94-101.
Panza Francesco et al: "Development of disease-modifying drugs for frontotemporal dementia spectrum disorders", Nature Reviews Neurology, Nature Publishing Group UK, London, vol. 16, No. 4, Mar. 23, 2020 (Mar. 23, 2020), pp. 213-228.
Ping Fang et al: "HMGB1 in Development and Diseases of the Central Nervous System", Molecular Neurobiology, Humana Press Inc, New York, vol. 45, No. 3, May 13, 2012 (May 13, 2012), pp. 499-506.
Okazawa, Hitoshi et al. "Novel insights of synapse pathology in neurodegenerative diseases" Monthly Cells 2018. vol. 50, No. 14. pp. 25-28. [Substitute English Translation].
Okazawa, Hitoshi et al. "Novel insights of synapse pathology in neurodegenerative diseases" Monthly Cells 2018. vol. 50, No. 14. pp. 25-28.
International Search Report, PCT/JP2021/044619 dated Feb. 1, 2022.

* cited by examiner

*Primary Examiner* — Sean E Aeder
(74) *Attorney, Agent, or Firm* — Edwin S. Flores; Daniel J. Chalker; Chalker Flores, LLP

(57) ABSTRACT

An object of the present invention is to provide an agent for preventing or treating frontotemporal lobar degeneration which does not cause noticeable adverse reactions and exhibits an excellent effect of preventing and treating frontotemporal lobar degeneration caused by different factors. In the present invention, a human monoclonal antibody that specifically binds to human HMGB1, which comprises heavy chain CDR1, heavy chain CDR2, and heavy chain CDR3 each consisting of a specific amino acid sequence and light chain CDR1, light chain CDR2, and light chain CDR3 each consisting of a specific amino acid sequence, can be used as an agent for preventing or treating frontotemporal lobar degeneration.

8 Claims, 11 Drawing Sheets

Specification includes a Sequence Listing.

AGENT FOR PREVENTING OR TREATING FRONTOTEMPORAL LOBAR DEGENERATION

CROSS-REFERENCE TO RELATED APPLICATIONS

This application is the National Stage of International Application No. PCT/JP2021/044619, filed on Dec. 6, 2021, claiming the priority of JP 2020-204343, filed on Dec. 9, 2020, the content of each of which is incorporated by reference herein.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on May 26, 2023, is named HRTA1058US_SeqList.txt and is 11, kilobytes in size.

TECHNICAL FIELD

The present invention relates to a drug product for preventing or treating frontotemporal lobar degeneration (FTLD).

BACKGROUND ART

Frontotemporal lobar degeneration is the second or third most common early-onset neurodegenerative dementia following Alzheimer's disease and is considered closely related to motor neuron diseases. Frontotemporal lobar degeneration has symptoms of noticeable changes in behavior and personality which are often accompanied by language impairment, and these symptoms gradually progress to cognitive impairment and dementia. As causative genes of familial frontotemporal lobar degeneration, valosin-containing protein (VCP), progranulin (PGRN), charged multivesicular body protein 2B (CHMP2B), and transactive response DNA-binding protein of 43 kD (TDP-43) are known. Studies of frontotemporal lobar degeneration are under way, but the whole picture of the onset mechanism thereof is yet to be clarified as with Alzheimer's disease.

Further, studies of therapeutic agents for frontotemporal lobar degeneration are also under way. For example, it has been reported that an inhibitor of Src/c-Abl, which is a tyrosine kinase, has an effect of improving the viability of cortical neurons derived from patients with frontotemporal lobar degeneration (Patent Document 1). Further, the present inventors have reported that, when vemurafenib, an inhibitor of b-RAF, which is a serine/threonine kinase, was administered to PGRN$^{R504X}$-KI mice (FTLD model mice), which have a stop codon for arginine (R) at position 504 of PGRN, behavioral anomalies observed in PGRN$^{R504X}$-KI mice were improved (Patent Document 2). At this point, however, there is no radical treatment for frontotemporal lobar degeneration. Further, unlike Alzheimer's disease, even therapeutic agents for improving symptoms of frontotemporal lobar degeneration have not been adequately developed.

Meanwhile, high mobility group box 1 (HMGB1) protein is known as one of non-histone chromatin-associated proteins that are involved in maintenance of the DNA structure and transcriptional regulation. Recently, this HMGB1 is drawing attention because it not only functions in the nucleus but also functions as a so-called damage-associated molecule pattern (DAMP) when it is released out of a cell owing to cellular necrosis or actively secreted out of a cell owing to a vascular inflammatory response to a signal. The present inventors found that, in Alzheimer's disease, HMGB1 leaking out of a cell owing to neuronal necrosis induces phosphorylation of serine at position 46 (Ser46) of MARCKS, which is a substrate of a phosphorylating enzyme, thereby inducing degeneration of neurites, prepared a mouse monoclonal antibody against HMGB1, and found that this mouse monoclonal antibody inhibits phosphorylation of Ser46 of MARCKS (Non-Patent Document 1). Further, the present inventors have reported that this mouse monoclonal antibody and a human monoclonal antibody resolve cognitive impairment in Alzheimer's disease model mice (Patent Documents 3 and 4).

PRIOR ART DOCUMENTS

Patent Documents

Patent Document 1: International Publication No. WO 2018/216705
Patent Document 2: International Publication No. WO 2015/099094
Patent Document 3: International Publication No. WO 2018/030405
Patent Document 4: International Publication No. WO 2020/059847

Non-Patent Document

Non Patent Document 1: SCIENTIFIC REPORT, Aug. 25, 2016; 6:31895

SUMMARY OF THE INVENTION

Object to be Solved by the Invention

An object of the present invention is to provide an agent for preventing or treating frontotemporal lobar degeneration which does not cause noticeable adverse reactions and exhibits an excellent effect of preventing and treating frontotemporal lobar degeneration caused by different factors.

Means to Solve the Object

The present inventors are continuing to study assiduously to solve the above-described object. During this process, they found that, when the human monoclonal antibody #129 prepared in the examples of International Publication No. WO 2020/059847 (Patent Document 4) was administered to four types of FTLD model mice each having a different causative gene, specifically, a mouse in which threonine (T) at position 262 is substituted with alanine (A) in VCP (VCP$^{T262A}$-KI mouse), a mouse which has a stop codon for arginine (R) at position 504 in PGRN (PGRN$^{R504X}$-KI mouse), a mouse which has a stop codon for glutamine (Q) at position 165 in CHMP2B (CHMP2B$^{Q165X}$-KI mouse), and a mouse in which asparagine (N) at position 267 is substituted with serine (S) in TDP-43 (TDP-43$^{N267S}$-KI mouse), decreased cognitive function and nerve damage-associated symptoms caused by FTLD could be effectively prevented and improved in all these FTLD model mice without causing noticeable adverse reactions, and thus accomplished the present invention.

Specifically, the present invention provides the following.

[1] An agent for preventing or treating frontotemporal lobar degeneration, comprising a human monoclonal antibody that specifically binds to human HMGB1 and comprises:

a heavy chain complementarity determining region (CDR) 1 consisting of the amino acid sequence shown in SEQ ID No: 1 or an amino acid sequence in which one or more amino acids are substituted, deleted, added, and/or inserted in the amino acid sequence shown in SEQ ID No: 1; a heavy chain CDR2 consisting of the amino acid sequence shown in SEQ ID No: 2 or an amino acid sequence in which one or more amino acids are substituted, deleted, added, and/or inserted in the amino acid sequence shown in SEQ ID No: 2; and a heavy chain CDR3 consisting of the amino acid sequence shown in SEQ ID No: 3 or an amino acid sequence in which one or more amino acids are substituted, deleted, added, and/or inserted in the amino acid sequence shown in SEQ ID No: 3; and a light chain CDR1 consisting of the amino acid sequence shown in SEQ ID No: 4 or an amino acid sequence in which one or more amino acids are substituted, deleted, added, and/or inserted in the amino acid sequence shown in SEQ ID No: 4; a light chain CDR2 consisting of the amino acid sequence shown in SEQ ID No: 5 or an amino acid sequence in which one or more amino acids are substituted, deleted, added, and/or inserted in the amino acid sequence shown in SEQ ID No: 5; and a light chain CDR3 consisting of an amino acid sequence shown in SEQ ID No: 6 or an amino acid sequence in which one or more amino acids are substituted, deleted, added, and/or inserted in the amino acid sequence shown in SEQ ID No: 6.

[2] The agent according to the above-described [1], wherein the human monoclonal antibody comprises a heavy chain variable region consisting of an amino acid sequence having at least 80% or more sequence identity to the amino acid sequence shown in SEQ ID No: 7, and a light chain variable region consisting of an amino acid sequence having at least 80% or more sequence identity to the amino acid sequence shown in SEQ ID No: 8.

[3] The agent according to the above-described [1] or [2], wherein the human monoclonal antibody comprises a heavy chain consisting of an amino acid sequence having at least 80% or more sequence identity to the amino acid sequence shown in SEQ ID No: 9, and a light chain consisting of an amino acid sequence having at least 80% or more sequence identity to the amino acid sequence shown in SEQ ID No: 10.

[4] The agent according to any of the above-described [1] to [3], wherein the agent is intravenously administered.

Further, examples of other embodiments of the present invention include the following:

a method for preventing or treating frontotemporal lobar degeneration, comprising a step of administering a human monoclonal antibody that specifically binds to human HMGB1 and comprises:

a heavy chain complementarity determining region (CDR)1 consisting of an amino acid sequence shown in SEQ ID No: 1 or an amino acid sequence in which one or more amino acids are substituted, deleted, added, and/or inserted in the amino acid sequence shown in SEQ ID No: 1, a heavy chain CDR2 consisting of an amino acid sequence shown in SEQ ID No: 2 or an amino acid sequence in which one or more amino acids are substituted, deleted, added, and/or inserted in the amino acid sequence shown in SEQ ID No: 2, and a heavy chain CDR3 consisting of an amino acid sequence shown in SEQ ID No: 3 or an amino acid sequence in which one or more amino acids are substituted, deleted, added, and/or inserted in the amino acid sequence shown in SEQ ID No: 3; and a light chain CDR1 consisting of an amino acid sequence shown in SEQ ID No: 4 or an amino acid sequence in which one or more amino acids are substituted, deleted, added, and/or inserted in the amino acid sequence shown in SEQ ID No: 4, a light chain CDR2 consisting of an amino acid sequence shown in SEQ ID No: 5 or an amino acid sequence in which one or more amino acids are substituted, deleted, added, and/or inserted in the amino acid sequence shown in SEQ ID No: 5, and a light chain CDR3 consisting of an amino acid sequence shown in SEQ ID No: 6 or an amino acid sequence in which one or more amino acids are substituted, deleted, added, and/or inserted in the amino acid sequence shown in SEQ ID No: 6 (hereinafter may be referred to as "the human monoclonal antibody of the present invention"), to a subject in need of the prevention or treatment of frontotemporal lobar degeneration; the human monoclonal antibody of the present invention for use as an agent for preventing or treating frontotemporal lobar degeneration;

the human monoclonal antibody of the present invention for use in prevention or treatment of frontotemporal lobar degeneration; and use of the human monoclonal antibody of the present invention for manufacturing an agent for preventing or treating frontotemporal lobar degeneration.

Effect of the Invention

When the human monoclonal antibody of the present invention is used, symptoms of frontotemporal lobar degeneration caused by different causative genes, specifically, $VCP^{T262A}$, $PGRN^{R504X}$, $CHMP2B^{Q165X}$, and TDP-$43^{N267S}$, can be effectively prevented or treated without causing noticeable adverse reactions. Therefore, an agent for preventing or treating frontotemporal lobar degeneration comprising the human monoclonal antibody of the present invention as an active ingredient is well expected to exhibit an excellent effect of preventing and treating frontotemporal lobar degeneration caused by various factors.

BRIEF DESCRIPTION OF DRAWINGS

FIG. 2-1 shows the results of an immunohistochemical staining analysis of pSer46-MARCKS levels in the cerebral cortex in four types of FTLD model mice ($VCP^{T262A}$-KI mice [FIG. 2-1A], $PGRN^{R504X}$-KI mice [FIG. 2-1B], $CHMP2B^{Q165X}$-KI mice [FIG. 2-1C], and TDP-$43^{N267S}$-KI mice [FIG. 2-1D]). Of note, all the similarly quantified pSer46-MARCKS levels in C57BL/6J mice were 0 (zero).

FIG. 2-2 shows the results of a Nissl's staining analysis of the brain tissue in two types of FTLD model mice ($VCP^{T262A}$-KI mice [FIG. 2-2A] and $PGRN^{R504X}$-KI mice [FIG. 2-2B]). The arrow in the left image points at a vacuole.

The right image is a highly magnified image of the region pointed at by the black arrow in the left image.

Figure 3A:
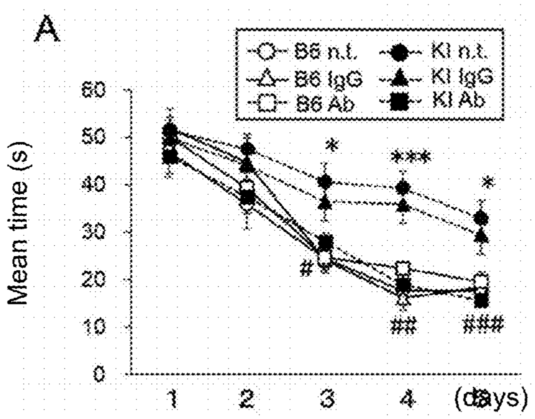
Figure 3B:
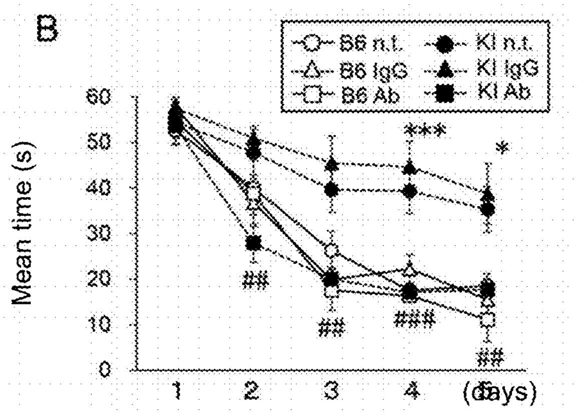
Figure 3C:
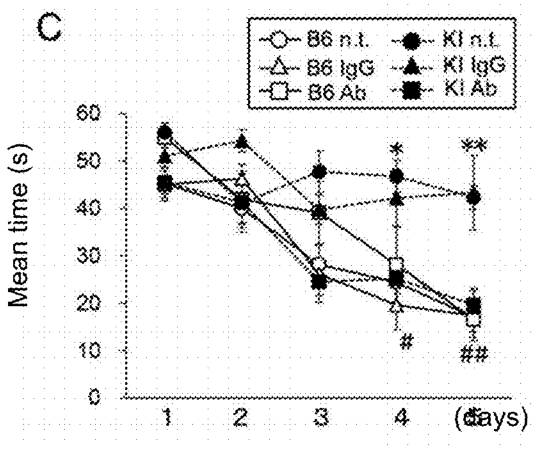
Figure 3D:
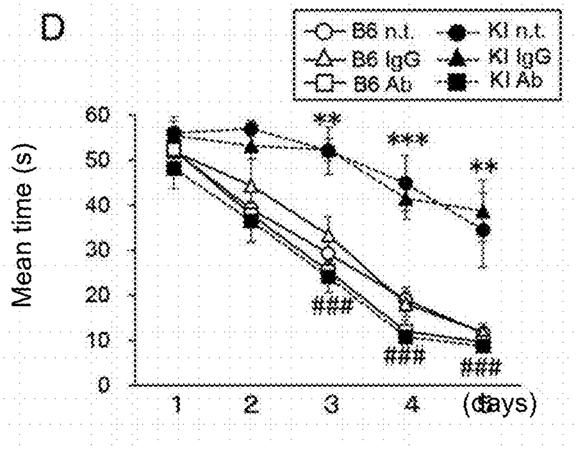
Figure 4A:
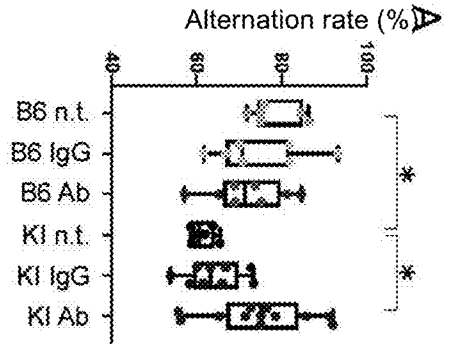
Figure 4B:
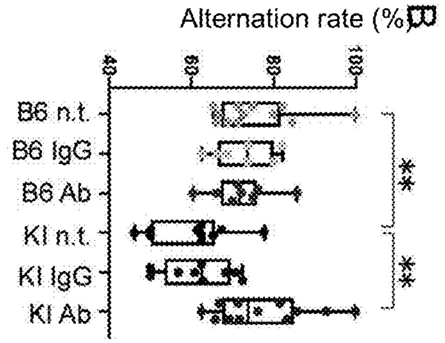
Figure 4C:
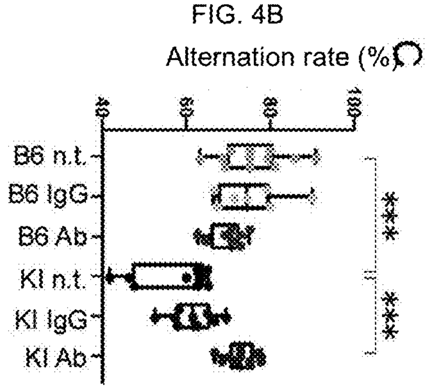
Figure 4D:
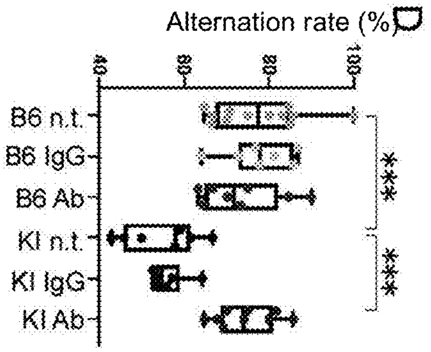

FIG. 3A shows the results of a Morris water maze test performed at one to five days from 10 months of age in TDP-$43^{N267S}$-KI mice ("KI Ab" in the figure [n=12]) and C57BL/6J mice ("B6 Ab" in the figure [n=8]) to which the human monoclonal antibody #129 of the present invention was administered, TDP-$43^{N267S}$-KI mice ("KI IgG" in the figure [n=11]) and C57BL/6J mice ("B6 IgG" in the figure [n=6]) to which a control human IgG was administered, and TDP-$43^{N267S}$-KI mice ("KI n.t." in the figure [n=10]) and C57BL/6J mice ("B6 n.t." in the figure [n=6]) which were not treated. FIG. 3B shows the results of a Morris water maze test performed at one to five days from seven months of age in $PGRN^{R504X}$-KI mice ("KI Ab" in the figure [n=11]) and C57BL/6J mice ("B6 Ab" in the figure [n=6]) to which the human monoclonal antibody #129 of the present invention was administered, $PGRN^{R504X}$-KI mice ("KI IgG" in the figure [n=7]) and C57BL/6J mice ("B6 IgG" in the figure [n=7]) to which a control human IgG was administered, and $PGRN^{R504X}$-KI mice ("KI n.t." in the figure [n=11]) and C57BL/6J mice ("B6 n.t." in the figure [n=7]) which were not treated. FIG. 3C shows the results of a Morris water maze test performed at one to five days from 10 months of age in $VCP^{T262A}$-KI mice ("KI Ab" in the figure [n=13]) and C57BL/6J mice ("B6 Ab" in the figure [n=6]) to which the human monoclonal antibody #129 of the present invention was administered, $VCP^{T262A}$-KI mice ("KI IgG" in the figure [n=5]) and C57BL/6J mice ("B6 IgG" in the figure [n=7]) to which a control human IgG was administered, and $VCP^{T262A}$-KI mice ("KI n.t." in the figure [n=7]) and C57BL/6J mice ("B6 n.t." in the figure [n=6]) which were not treated. FIG. 3D shows the results of a Morris water maze test performed at one to five days from six months of age in $CHMP2B^{Q165X}$-KI mice ("KI Ab" in the figure [n=7]) and C57BL/6J mice ("B6 Ab" in the figure [n=6]) to which the human monoclonal antibody #129 of the present invention was administered, $CHMP2B^{Q165X}$-KI mice ("KI IgG" in the figure [n=5]) and C57BL/6J mice ("B6 IgG" in the figure [n=7]) to which a control human IgG was administered, and $CHMP2B^{Q165X}$-KI mice ("KI n.t." in the figure [n=5]) and C57BL/6J mice ("B6 n.t." in the figure [n=6]) which were not treated. In the figures, "*," "," and "*" indicate that the results of "KI n.t." showed a statistically significant difference from those of "B6 n.t." in a Tukey's HSD test ($p<0.05$, $p<0.01$, and $p<0.001$, respectively). Further, in the figures, "#," "##," and "###" indicate that the results of "KI Ab" showed a statistically significant difference from those of "KI n.t." in a Tukey's HSD test ($p<0.05$, $p<0.01$, and $p<0.001$, respectively).

FIG. 4 shows the results of a Y-maze test performed at seven months of age (FIG. 4A), eight months of age (FIG. 4B), nine months of age (FIG. 4C), and 10 months of age (FIG. 4D) in TDP-$43^{N267S}$-KI mice ("KI Ab" in the figures [n=12 (FIGS. 4A to 4C); n=9 (FIG. 4D)]) and C57BL/6J mice ("B6 Ab" in the figures [n=8 (FIGS. 4A to 4D)]) to which the human monoclonal antibody #129 of the present invention was administered, TDP-$43^{N267S}$-KI mice ("KI IgG" in the figures [n=9 (FIGS. 4A to 4C); n=6 (FIG. 4D)]) and C57BL/6J mice ("B6 IgG" in the figures [n=7 (FIGS. 4A to 4D)]) to which a control human IgG was administered, and TDP-$43^{N267S}$-KI mice ("KI n.t." in the figures [n=6 (FIG. 4A); n=10 (FIG. 4B); n=9 (FIG. 4C); n=7 (FIG. 4D)]) and C57BL/6J mice ("B6 n.t." in the figures [n=6 (FIG. 4A); n=12 (FIGS. 4B to 4D)]) which were not treated. In the figures, "*," "," and "*" indicate that a statistically significant difference was detected in a Tukey's HSD test ($p<0.05$, $p<0.01$, and $p<0.001$, respectively) (hereunder, same in FIGS. 5 to 16).

Figure 5A:
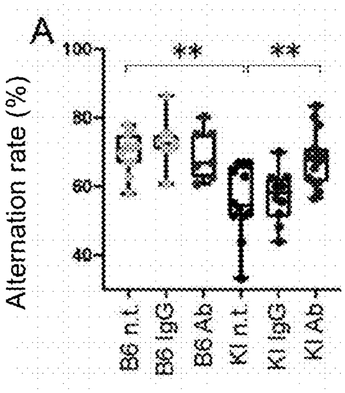
Figure 5B:
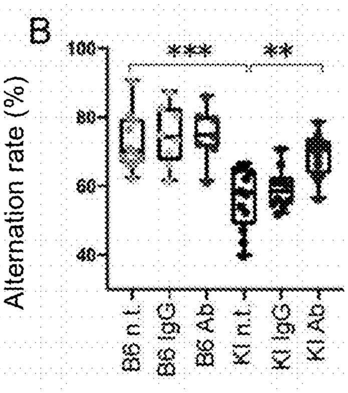
Figure 5C:
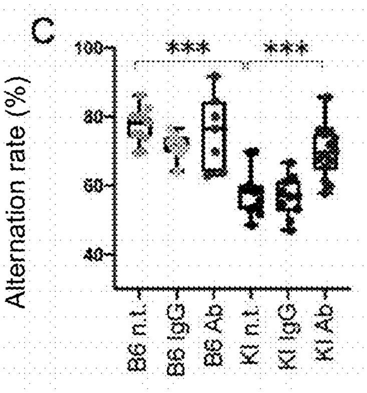
Figure 6A:
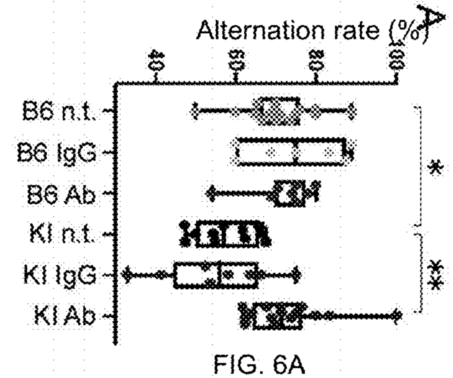
Figure 6B:
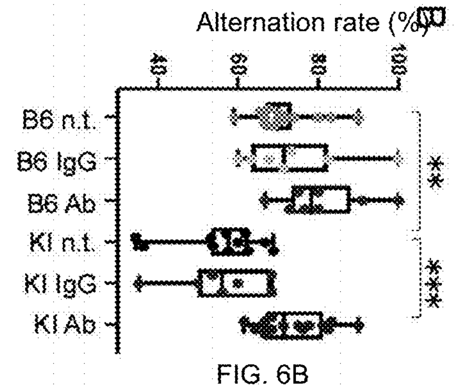
Figure 6C:
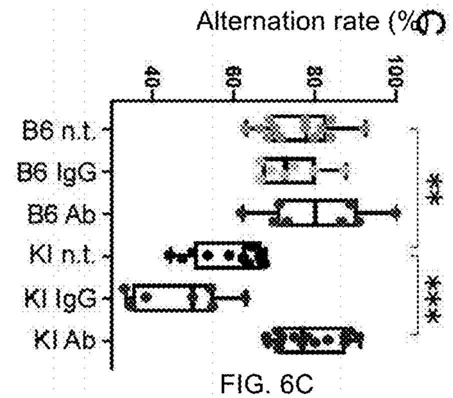
Figure 6D:
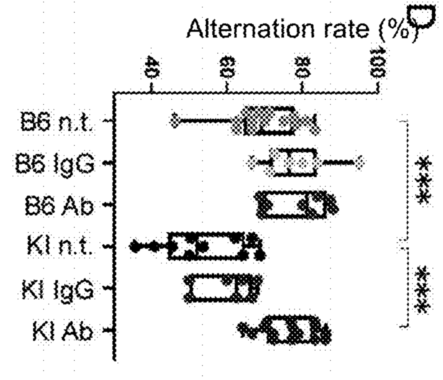

FIG. 5 shows the results of a Y-maze test performed at five months of age (FIG. 5A), six months of age (FIG. 5B), and seven months of age (FIG. 5C) in $PGRN^{R504X}$-KI mice ("KI Ab" in the figures [n=15 (FIGS. 5A and 5B); n=14 (FIG. 5C)]) and C57BL/6J mice ("B6 Ab" in the figures [n=7 (FIGS. 5A to 5C)]) to which the human monoclonal antibody #129 of the present invention was administered, $PGRN^{R504X}$-KI mice ("KI IgG" in the figures [n=10 (FIGS. 5A to 5C)]) and C57BL/6J mice ("B6 IgG" in the figures [n=8 (FIGS. 5A to 5C)]) to which a control human IgG was administered, and $PGRN^{R504X}$-KI mice ("KI n.t." in the figures [n=11 (FIGS. 5A and 5C); n=12 (FIG. 5B)]) and C57BL/6J mice ("B6 n.t." in the figure [n=7 (FIG. 5A); n=11 (FIGS. 5B and 5C)]) which were not treated.

FIG. 6 shows the results of a Y-maze test performed at seven months of age (FIG. 6A), eight months of age (FIG. 6B), nine months of age (FIG. 6C), and 10 months of age (FIG. 6D) in $VCP^{T262A}$-KI mice ("KI Ab" in the figures [n=15 (FIGS. 6A to 6C); n=12 (FIG. 6D)]) and C57BL/6J mice ("B6 Ab" in the figures [n=8 (FIGS. 6A to 6C); n=5 (FIG. 6D)]) to which the human monoclonal antibody #129 of the present invention was administered, $VCP^{T262A}$-KI mice ("KI IgG" in the figures [n=8 (FIG. 6A); n=7 (FIGS. 6B and 6C); n=5 (FIG. 6D)]) and C57BL/6J mice ("B6 IgG" in the figures [n=7 (FIGS. 6A to 6C); n=6 (FIG. 6D)]) to which a control human IgG was administered, and $VCP^{T262A}$-KI mice ("KI n.t." in the figures [n=11 (FIGS. 6A to 6C); n=5 (FIG. 6D)]) and C57BL/6J mice ("B6 n.t." in the figures [n=17 (FIG. 6A); n=16 (FIG. 6B); n=13 (FIG. 6C); n=12 (FIG. 6D)]) which were not treated.

Figure 7A:
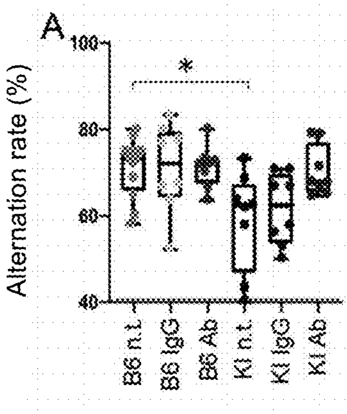
Figure 7B:
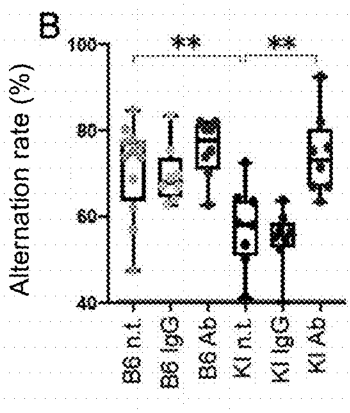
Figure 7C:
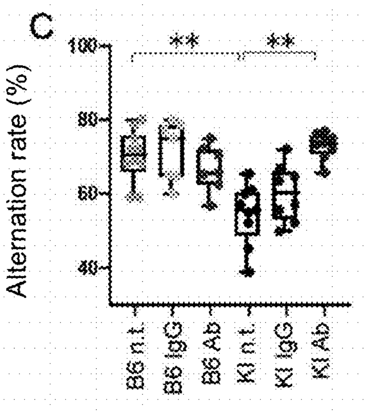

FIG. 7 shows the results of a Y-maze test performed at four months of age (FIG. 7A), five months of age (FIG. 7B), and six months of age (FIG. 7C) in $CHMP2B^{Q165X}$-KI mice ("KI Ab" in the figures [n=8 (FIGS. 7A to 7C)]) and C57BL/6J mice ("B6 Ab" in the figures [n=8 (FIGS. 7A to 7C)]) to which the human monoclonal antibody #129 of the present invention was administered, $CHMP2B^{Q165X}$-KI mice ("KI IgG" in the figures [n=8 (FIGS. 7A to 7C)]) and C57BL/6J mice ("B6 IgG" in the figures [n=8 (FIGS. 7A to 7C)]) to which a control human IgG was administered, and $CHMP2B^{Q165X}$-KI mice ("KI n.t." in the figures [n=8 (FIGS. 7A to 7C)]) and C57BL/6J mice ("B6 n.t." in the figures [n=12 (FIG. 7A); n=10 (FIG. 7B); n=10 (FIG. 7C)]) which were not treated.

Figure 8A:
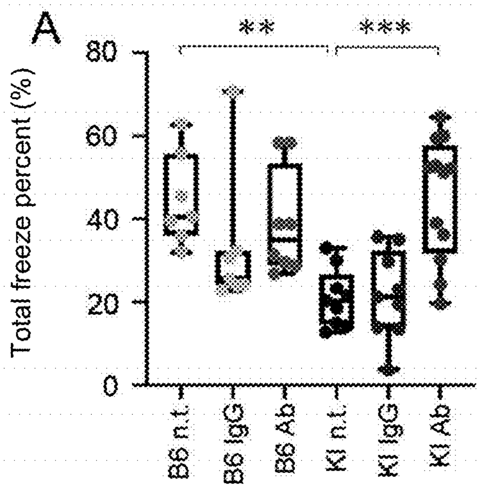
Figure 8B:
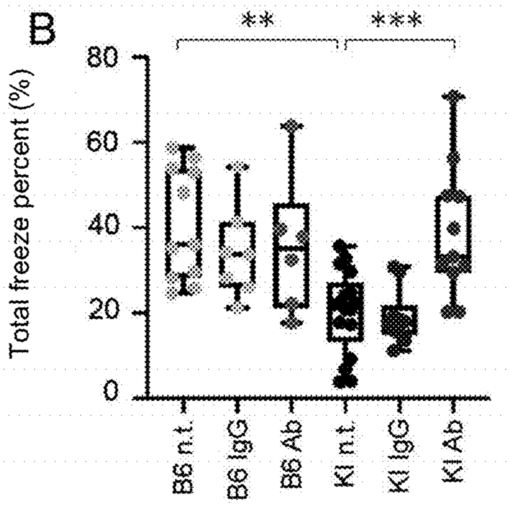
Figure 8C:
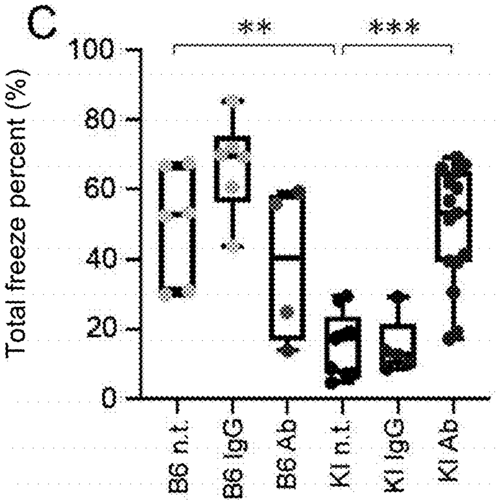
Figure 8D:
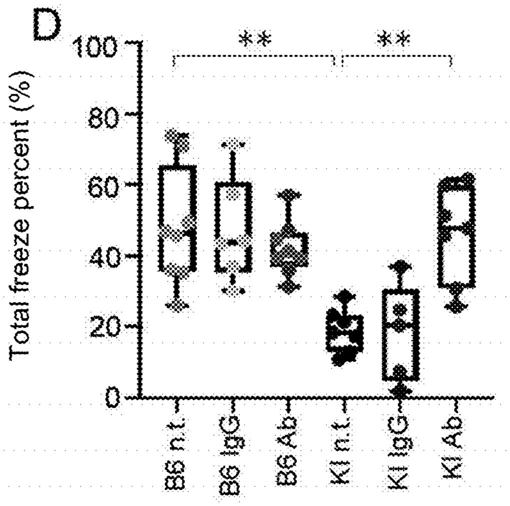
Figure 9A:
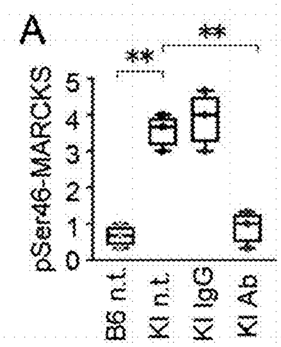
Figure 9B:
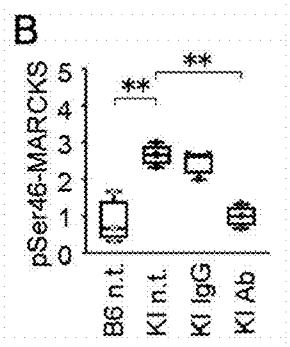
Figure 9C:
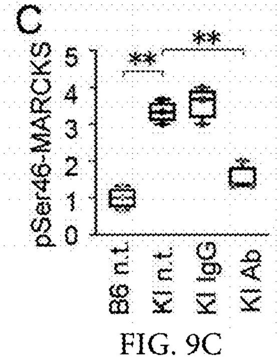
Figure 9D:
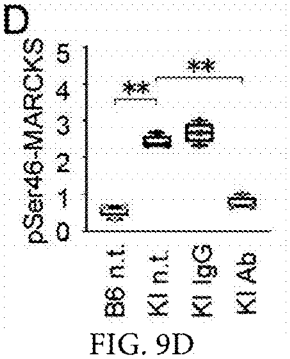
Figure 10A:
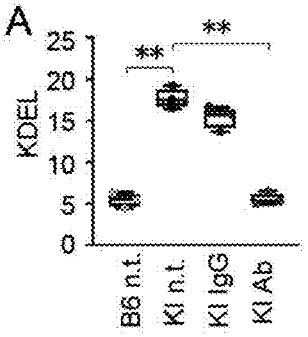
Figure 10B:
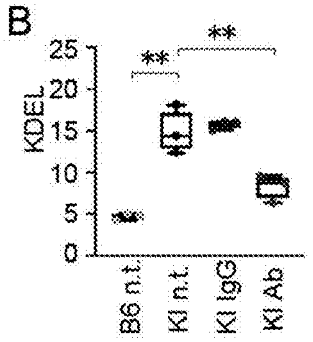
Figure 10C:
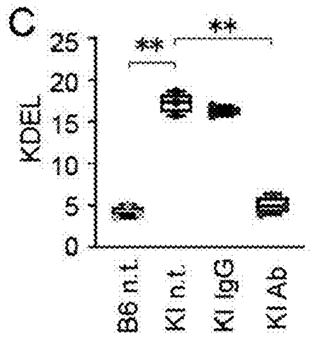
Figure 10D:
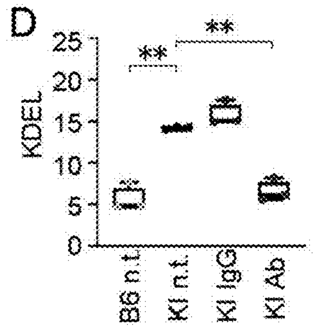
Figure 11A:
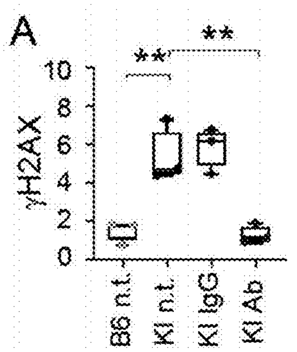
Figure 11B:
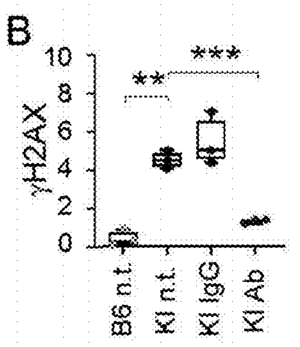
Figure 11C:
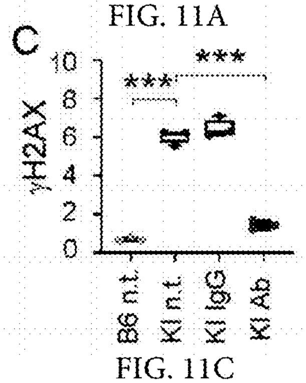
Figure 11D:
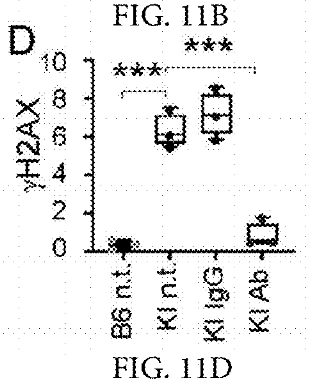
Figure 12A:
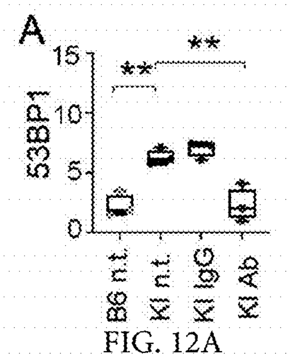
Figure 12B:
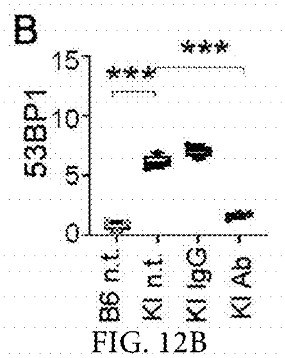
Figure 12C:
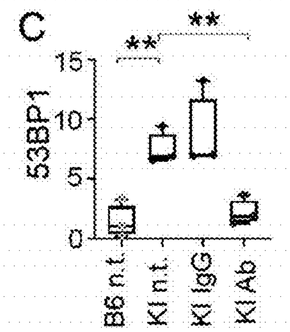
Figure 12D:
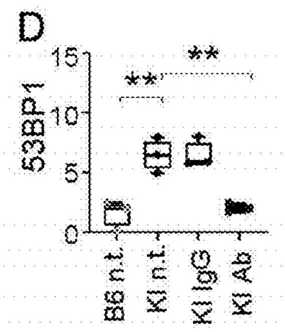
Figure 13A:
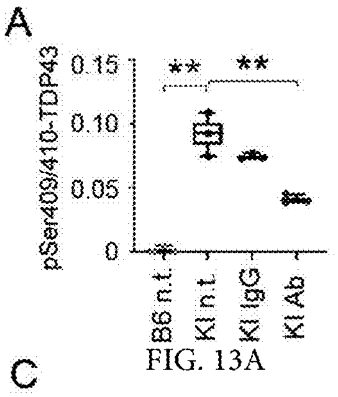
Figure 13B:
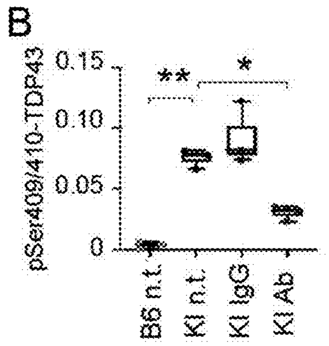
Figure 13C:
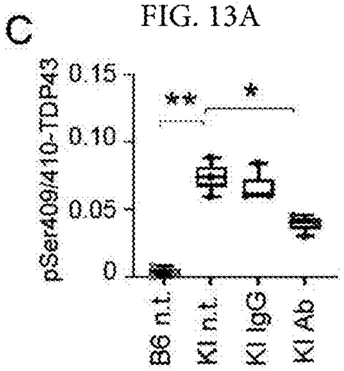
Figure 13D:
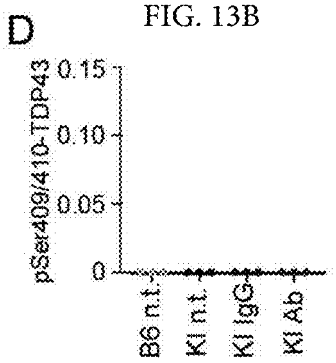
Figure 14A:
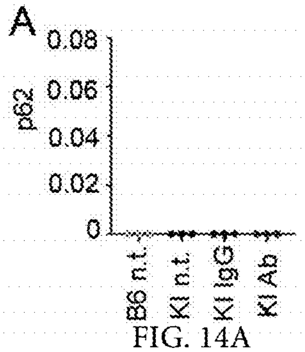
Figure 14B:
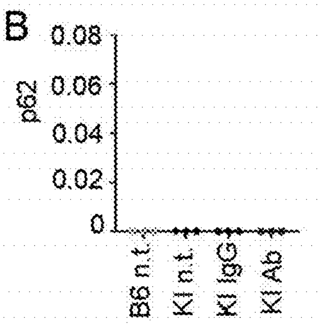
Figure 14C:
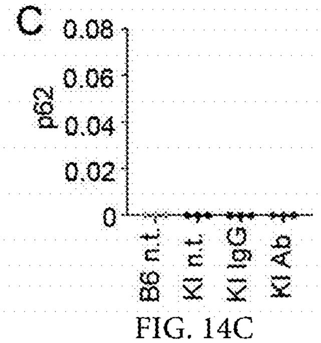
Figure 14D:
Figure 15A:
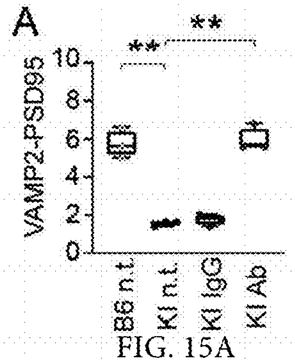
Figure 15B:
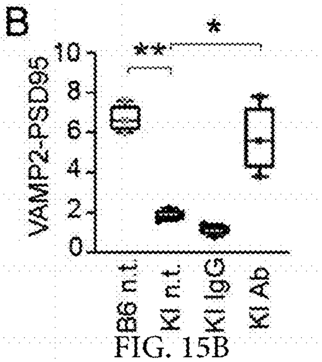
Figure 15C:
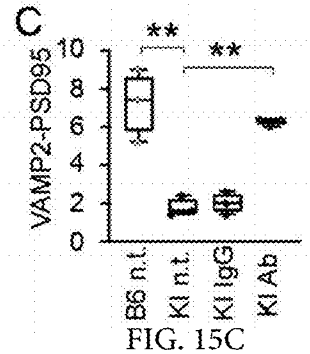
Figure 15D:
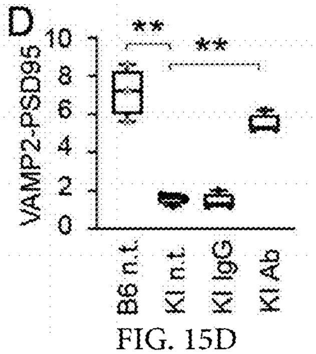
Figure 16A:
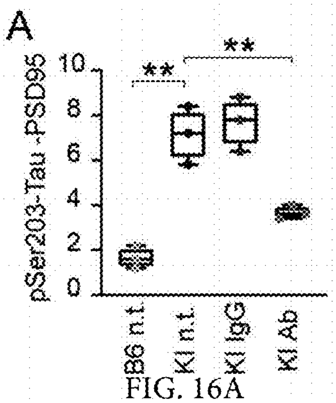
Figure 16B:
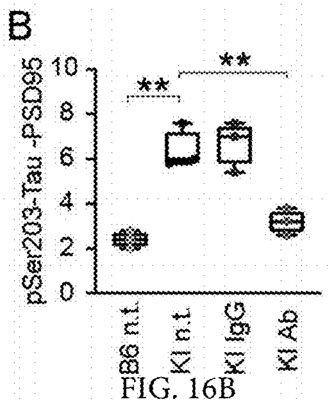
Figure 16C:
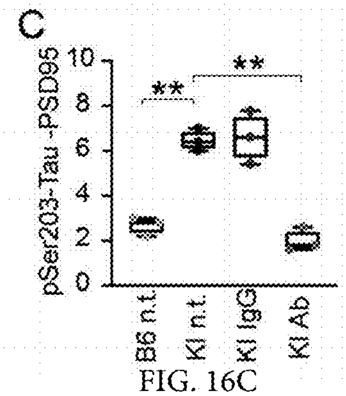
Figure 16D:
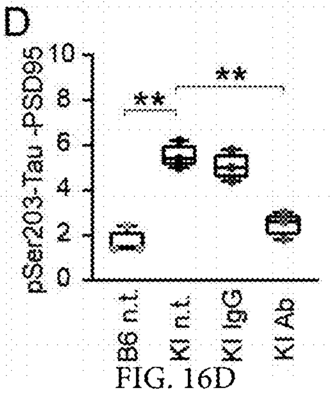

FIG. 8A shows the results of a fear-conditioning test performed at 10 months of age in TDP-$43^{N267S}$-KI mice ("KI Ab" in the figure [n=12]) and C57BL/6J mice ("B6 Ab" in the figure [n=8]) to which the human monoclonal antibody #129 of the present invention was administered, TDP-$43^{N267S}$-KI mice ("KI IgG" in the figure [n=9]) and C57BL/6J mice ("B6 IgG" in the figure [n=7]) to which a control human IgG was administered, and TDP-$43^{N267S}$-KI mice ("KI n.t." in the figure [n=9]) and C57BL/6J mice ("B6 n.t." in the figure [n=7]) which were not treated. FIG. 8B shows the results of a fear-conditioning test performed at seven months of age in $PGRN^{R504X}$-KI mice ("KI Ab" in the figure [n=11]) and C57BL/6J mice ("B6 Ab" in the figure [n=6]) to which the human monoclonal antibody #129 of the present invention was administered, $PGRN^{R504X}$-KI mice ("KI IgG" in the figure [n=10]) and C57BL/6J mice ("B6 IgG" in the figure [n=7]) to which a control human IgG was administered, and $PGRN^{R504X}$-KI mice ("KI n.t." in the figure [n=17]) and C57BL/6J mice ("B6 n.t." in the figure [n=11]) which were not treated. FIG. 8C shows the results of a fear-conditioning test performed at 10 months of age in $VCP^{T262A}$-KI mice ("KI Ab" in the figure [n=15]) and C57BL/6J mice ("B6 Ab" in the figure [n=4]) to which the human monoclonal antibody #129 of the present invention was administered, $VCP^{T262A}$-KI mice ("KI IgG" in the figure [n=5]) and C57BL/6J mice ("B6 IgG" in the figure [n=6]) to which a control human IgG was administered, and $VCP^{T262A}$-KI mice ("KI n.t." in the figure [n=9]) and C57BL/6J mice ("B6 n.t." in the figure [n=6]) which were not treated. FIG. 8D shows the results of a fear-conditioning test performed at six months of age in $CHMP2B^{Q165X}$-KI mice ("KI Ab" in the figure [n=7]) and C57BL/6J mice ("B6 Ab" in the figure [n=8]) to which the human monoclonal antibody #129 of the present invention was administered, $CHMP2B^{Q165X}$-KI mice ("KI IgG" in the figure [n=5]) and C57BL/6J mice ("B6 IgG" in the figure [n=6]) to which a control human IgG was administered, and $CHMP2B^{Q165X}$-KI mice ("KI n.t." in the figure [n=7]) and C57BL/6J mice ("B6 n.t." in the figure [n=8]) which were not treated.

FIG. 9 shows the results (n=3) of an immunohistochemical staining analysis of pSer46-MARCKS levels in the cerebral cortex in four types of FTLD model mice ($PGRN^{R504X}$-KI mice [FIG. 9A], TDP-$43^{N267S}$-KI mice [FIG. 9B], $VCP^{T262A}$-KI mice [FIG. 9C], and $CHMP2B^{Q165X}$-KI mice [FIG. 9D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and $CHMP2B^{Q165X}$-KI mice), seven months of age (C57BL/6J mice and $PGRN^{R504X}$-KI mice), and 10 months of age (C57BL/6J mice, TDP-$43^{N267S}$-KI mice, and $VCP^{T262A}$-KI mice).

FIG. 10 shows the results (n=3) of an immunohistochemical staining analysis of KDEL fluorescence levels in the cerebral cortex in four types of FTLD model mice ($PGRN^{R504X}$-KI mice [FIG. 10A], TDP-$43^{N267S}$-KI mice [FIG. 10B], $VCP^{T262A}$-KI mice [FIG. 10C], and $CHMP2B^{Q165X}$-KI mice [FIG. 10D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figure), and C57BL/6J mice which were not treated ("B6 n.t." in the figures) at six months of age (C57BL/6J mice and $CHMP2B^{Q165X}$-KI mice), seven months of age (C57BL/6J mice and $PGRN^{R504X}$-KI mice), and 10 months of age (C57BL/6J mice, TDP-$43^{N267S}$-KI mice, and $VCP^{T262A}$-KI mice).

FIG. 11 shows the results (n=3) of an immunohistochemical staining analysis of γH2AX fluorescence levels in the cerebral cortex in four types of FTLD model mice ($PGRN^{R504X}$-KI mice [FIG. 11A], TDP-$43^{N267S}$-KI mice [FIG. 11B], $VCP^{T262A}$-KI mice [FIG. 11C], and $CHMP2B^{Q165X}$-KI mice [FIG. 11D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and $CHMP2B^{Q165X}$-KI mice), seven months of age (C57BL/6J mice and $PGRN^{R504X}$-KI mice), and 10 months of age (C57BL/6J mice, TDP-$43^{N267S}$-KI mice, and $VCP^{T262A}$-KI mice).

FIG. 12 shows the results (n=3) of an immunohistochemical staining analysis of 53BP1 fluorescence levels in the cerebral cortex in four types of FTLD model mice ($PGRN^{R504X}$-KI mice [FIG. 12A], TDP-$43^{N267S}$-KI mice [FIG. 12B], $VCP^{T262A}$-KI mice [FIG. 12C], and $CHMP2B^{Q165X}$-KI mice [FIG. 12D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and $CHMP2B^{Q165X}$-KI mice), seven months of age (C57BL/6J mice and $PGRN^{R504X}$-KI mice), and 10 months of age (C57BL/6J mice, TDP-$43^{N267S}$-KI mice, and $VCP^{T262A}$-KI mice).

FIG. 13 shows the results (n=3) of an immunohistochemical staining analysis of pSer409/410-TDP-43 fluorescence levels in the cerebral cortex in four types of FTLD model mice ($PGRN^{R504X}$-KI mice [FIG. 13A], TDP-$43^{N267S}$-KI mice [FIG. 13B], $VCP^{T262A}$-KI mice [FIG. 13C], and $CHMP2B^{Q165X}$-KI mice [FIG. 13D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and $CHMP2B^{Q165X}$-KI mice), seven months of age (C57BL/6J mice and $PGRN^{R504X}$-KI mice), and 10 months of age (C57BL/6J mice, TDP-$43^{N267S}$-KI mice, and $VCP^{T262A}$-KI mice).

FIG. 14 shows the results (n=3) of an immunohistochemical staining analysis of p62 fluorescence levels in the cerebral cortex in four types of FTLD model mice ($PGRN^{R504X}$-KI mice [FIG. 14A], TDP-$43^{N267S}$-KI mice [FIG. 14B], $VCP^{T262A}$-KI mice [FIG. 14C], and $CHMP2B^{Q165X}$-KI mice [FIG. 14D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and $CHMP2B^{Q165X}$-KI mice), seven months of age (C57BL/6J mice and $PGRN^{R504X}$-KI mice), and 10 months of age (C57BL/6J mice, TDP-$43^{N267S}$-KI mice, and $VCP^{T262A}$-KI mice).

FIG. 15 shows the results (n=3) of an immunohistochemical staining analysis of the proportion of cells having a VAMP2 fluorescence signal and a PSD95 fluorescence signal colocalized therein in the cerebral cortex in four types of FTLD model mice ($PGRN^{R504X}$-KI mice [FIG. 15A], TDP-$43^{N267S}$-KI mice [FIG. 15B], $VCP^{T262A}$-KI mice [FIG. 15C], and $CHMP2B^{Q165X}$-KI mice [FIG. 15D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and CHMP2B$^{Q165X}$-KI mice), seven months of age (C57BL/6J mice and PGRN$^{R504X}$-KI mice), and 10 months of age (C57BL/6J mice, TDP-43$^{N267S}$-KI mice, and VCP$^{T262A}$-KI mice).

FIG. 16 shows the results (n=3) of an immunohistochemical staining analysis of the proportion of cells having a pSer203-tau fluorescence signal and a PSD95 fluorescence signal colocalized therein in the cerebral cortex in four types of FTLD model mice (PGRN$^{R504X}$-KI mice [FIG. 16A], TDP-43$^{N267S}$-KI mice [FIG. 16B], VCP$^{T262A}$-KI mice [FIG. 16C], and CHMP2B$^{Q165X}$-KI mice [FIG. 16D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and CHMP2B$^{Q165X}$-KI mice), seven months of age (C57BL/6J mice and PGRN$^{R504X}$-KI mice), and 10 months of age (C57BL/6J mice, TDP-43$^{N267S}$-KI mice, and VCP$^{T262A}$-KI mice).

Figures 17A, 17B, 17C, 17D:
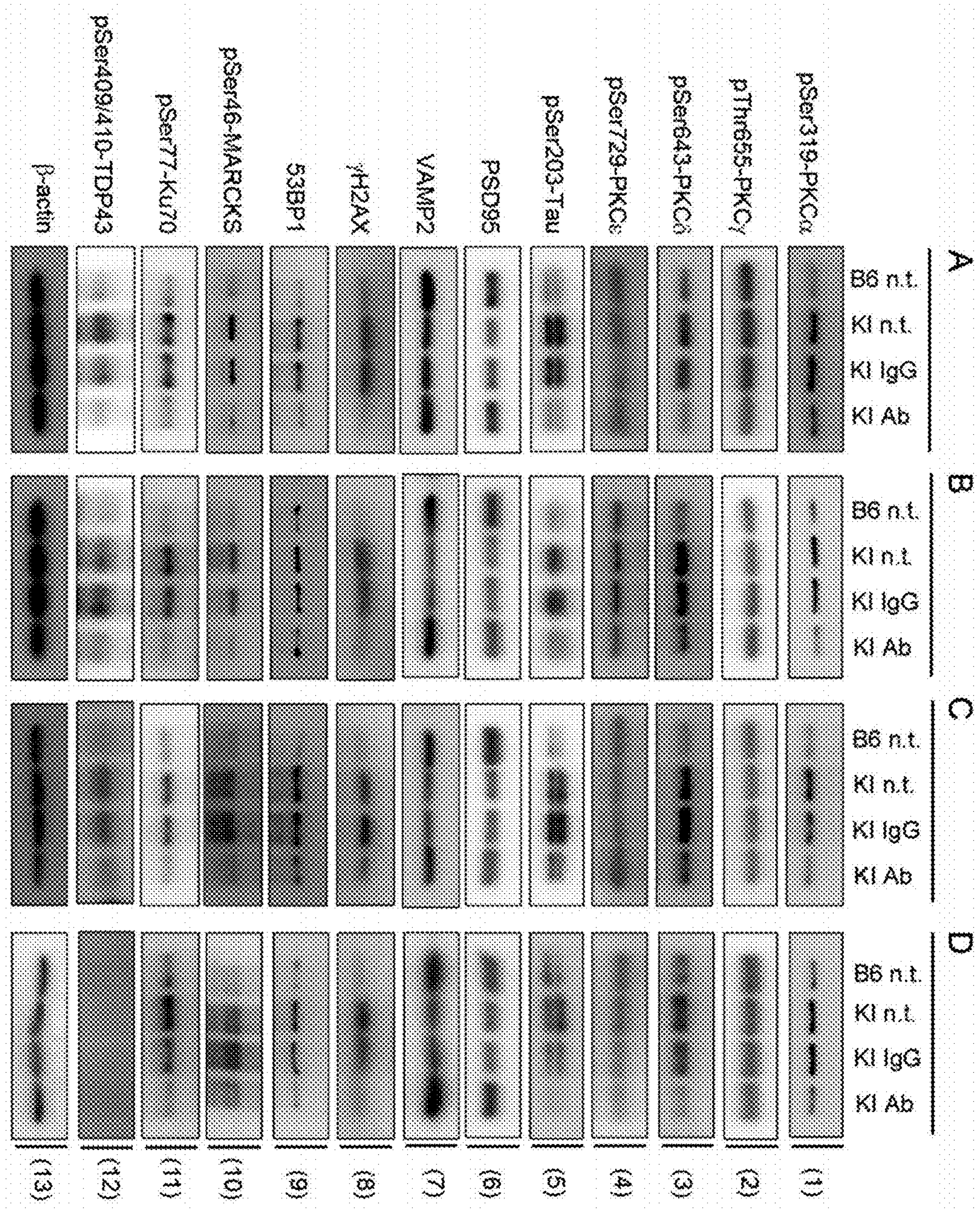

FIG. 17 shows the results of a Western blot analysis of the phosphorylation levels of four types of proteins associated with the core signaling in AD-FTLD (pSer319-PKCα, pThr655-PKCγ, pSer643-PKCδ, and pSer729-PKCε: Lanes (1) to (4), respectively), the phosphorylation level of one type of synapse instability-associated protein (pSer203-tau: Lane (5)), the expression levels of two types of synapse-associated proteins (PSD95 and VAMP2: Lanes (6) and (7), respectively), the expression levels of two types of DNA damage-associated proteins (γH2AX and 53BP1: Lanes (8) and (9), respectively), the phosphorylation level of one type of cell death-associated protein (pSer46-MARCKS: Lane (10)), the phosphorylation level of one type of DNA repair-associated protein (pSer77-Ku70: Lane (11)), the level of one type of protein agglutination marker (pSer409/410-TDP-43: Lane (12)), and the expression level of β-actin, which is an internal standard protein (Lane (13)), in the cerebral cortex in four types of FTLD model mice (TDP-43$^{N267S}$-KI mice [FIG. 17A], PGRN$^{R504X}$-KI mice [FIG. 17B], VCP$^{T262A}$-KI mice [FIG. 17C], and CHMP2B$^{Q165X}$-KI mice [FIG. 17D]) to which the human monoclonal antibody #129 of the present invention was administered ("KI Ab" in the figures), the four types of FTLD model mice to which a control human IgG was administered ("KI IgG" in the figures), the four types of FTLD model mice which were not treated ("KI n.t." in the figures), and C57BL/6J mice which were not treated ("B6 n.t." in the figures) at six months of age (C57BL/6J mice and CHMP2B$^{Q165X}$-KI mice), seven months of age (C57BL/6J mice and PGRN$^{R504X}$-KI mice), and 10 months of age (C57BL/6J mice, TDP-43$^{N267S}$-KI mice, and VCP$^{T262A}$-KI mice).

MODE OF CARRYING OUT THE INVENTION

The agent for preventing or treating frontotemporal lobar degeneration of the present invention is an agent comprising the human monoclonal antibody of the present invention (hereinafter may be referred to as "the agent for preventing or treating of the present invention") used for a specific purpose of "preventing or treating frontotemporal lobar degeneration." The agent for preventing or treating of the present invention may be used solely as a medicine (drug product) or may be used in a form of a composition (pharmaceutical composition) by further mixing additives.

As used herein, the term "frontotemporal lobar degeneration (FTLD)" means a non-Alzheimer's disease type neurodegenerative disease which presents with atrophy of the human frontal and temporal lobes at an early stage and progresses to whole brain atrophy at a late stage. The "frontotemporal lobar degeneration" is classified into three types of disease depending on the clinical features thereof. Specifically, the three types of the disease are frontotemporal dementia (FTD), progressive non-fluent aphasia (PNFA), and semantic dementia (SD). FTLD is further classified into four types of disease pathologically depending on the types of proteins accumulated as abnormal proteins in cells. Specifically, the four types of the disease are FTLD-Tau, FTLD-TDP, FTLD-UPS, and FTLD-FUS. Further, the "frontotemporal lobar degeneration" also includes "familial frontotemporal lobar degeneration" and "hereditary frontotemporal lobar degeneration," which are attributed to a gene mutation, and "sporadic frontotemporal lobar degeneration" caused by environment factors, such as lifestyle and stress.

The above-mentioned "FTLD-Tau" is classified into "3R Tau" type, "4R Tau" type, and "3/4R Tau" type depending on the number of repeats of the microtubule-binding region in the tau protein predominantly accumulated in cells. The "3R Tau" type diseases include FTLD with Pick cells (Pick's disease) and FTLD with a gene mutation in microtubule-associated protein tau (MAPT) (FTLD-17). The "4R Tau" type diseases include the corticobasal degeneration, progressive supranuclear palsy, multiple system tauopathy with dementia, argyrophilic grain dementia (argyrophilic grain disease), and FTLD with a MAPT gene mutation (FTLD-17). The "3/4R Tau" type diseases include dementia of the neurofibrillary tangle type and FTLD with a MAPT gene mutation (FTLD-17). Meanwhile, a group of FTLDs which are negative for tau and have a ubiquitin-positive inclusion are referred to as "FTLD-U" and include the above-mentioned FTLD-TDP, FTLD-UPS, and FTLD-FUS.

The above-mentioned "FTLD-TDP" means a disease positive for transactive response DNA-binding protein of 43 kD (TDP-43) among FTLD-U diseases, and this disease includes FTLD with a progranulin (PGRN) mutation, such as PGRN$^{R504X}$, sporadic FTLD-TDP/FTLD-U, FTLD with a TDP-43 mutation, such as TDP-43$^{N267S}$, FTLD with a valosin-containing protein (VCP) mutation, such as VCP$^{T262A}$, and FTLD linked to chromosome 9. Further, the above-mentioned "FTLD-FUS" means a disease negative for TDP-43 and positive for fused in sarcoma (FUS) among FTLD-U diseases, and this disease includes neuronal intermediate filament inclusion disease, atypical FTLD-U, basophilic inclusion disease, and FTLD with a FUS mutation.

Further, the above-mentioned "FTLD-UPS" means a disease which is one type of FTLD-U negative for TDP-43, and this disease includes FTLD with a mutation in charged multivesicular body protein 2B (CHMP2B), such as CHMP2B$^{Q165X}$.

As used herein, the expression "prevention of frontotemporal lobar degeneration" includes not only suppression of presence or development of frontotemporal lobar degeneration, but also delay of presence or onset time of frontotemporal lobar degeneration. Further, the expression "treatment of frontotemporal lobar degeneration" includes not only resolution or improvement of lesions and symptoms of frontotemporal lobar degeneration including accumulation of abnormal proteins in cells, but also suppression of progression of the disease.

As used herein, the expression "development of frontotemporal lobar degeneration" means development of symptoms such as appearance of memory disturbance, higher brain dysfunction (for example, aphasia, apraxia, agnosia, constructional apraxia), and personality change, which are assessed by clinical diagnosis, and/or development of brain atrophy assessed by image diagnosis. Further, as used herein, the expression "presence of frontotemporal lobar degeneration" also means a condition where a pathological change characteristic to frontotemporal lobar degeneration (for example, accumulation of abnormal proteins in cells) is observed although the symptoms have not developed.

As demonstrated in the example described later, the human monoclonal antibody of the present invention contained in the preventing or treating agent of the present invention has high affinity for human HMGB1 protein and has an effect of reducing or suppressing the phosphorylation level of serine at position 46 (Ser46) in MARCKS (pSer46-MARCKS). Therefore, frontotemporal lobar degeneration caused by HMGB1 and/or pSer46-MARCKS can be mentioned as a preferred example of frontotemporal lobar degeneration to be prevented or treated with the preventing or treating agent of the present invention.

The human monoclonal antibody of the present invention is preferably a human monoclonal antibody comprising a heavy (H) chain variable region consisting of an amino acid sequence having at least 80% or more sequence identity to an amino acid sequence shown in SEQ ID No: 7 and a light (L) chain variable region consisting of an amino acid sequence having at least 80% or more sequence identity to an amino acid sequence shown in SEQ ID No: 8, more preferably a human monoclonal antibody comprising a heavy chain consisting of an amino acid sequence having at least 80% or more sequence identity to an amino acid sequence shown in SEQ ID No: 9 and a light chain consisting of an amino acid sequence having at least 80% or more sequence identity to an amino acid sequence shown in SEQ ID No: 10.

As used herein, "high mobility group box 1 (HMGB1)" is a protein also called HMG1, HMG3, SBP-1, or HMG-1. Human-derived HMGB1 is typically a protein consisting of an amino acid sequence identified as NCBI reference sequence: NP_002119.1 (a protein encoded by the nucleotide sequence identified as NCBI reference sequence: NM_002128.5). However, the DNA sequence of the gene is mutated in nature (that is, non-artificially) by a mutation thereof or the like, and the amino acid sequence of the protein encoded thereby is also modified along with the mutation. Therefore, in addition to the protein consisting of the amino acid sequence identified by NCBI reference sequence: NP_002119.1, variants of this protein existing in nature also fall within the scope of HMGB1, to which the human monoclonal antibody of the present invention binds.

As used herein, the term "antibody that specifically binds to human HMGB1" means an antibody that recognizes and binds to human HMGB1 through a highly specific antigen-antibody recognition mechanism. The human monoclonal antibody of the present invention is preferably in an isolated condition. The term "isolated" used herein means that an antibody exists in a condition different from the condition in which it originally exists, achieved by extracting the antibody by artificial manipulation from the environment where it originally exists, expressing the antibody in an environment that is not the environment where it originally exists antibody, or the like. That is, the term "isolated antibody" does not include an antibody derived from a certain individual and contained in the body of the individual or in a tissue or body fluid (for example, blood, plasma, or serum) derived from the body without undergoing an external operation (artificial manipulation). Further, the human monoclonal antibody of the present invention is preferably an antibody produced from an organism or a cell prepared by artificial manipulation (for example, an antibody produced from hybridoma). The "antibody produced from an organism or a cell prepared by artificial manipulation" does not include an antibody produced from an organism or a B cell that exists naturally (not undergoing artificial manipulation).

As used herein, the term "monoclonal antibody" means an antibody (including a functional fragment of an antibody) obtained from a group of substantially uniform antibodies. A monoclonal antibody recognizes a single determinant on an antigen. The human monoclonal antibody of the present invention includes human immunoglobulin classes and subclasses, as well as forms of functional fragments of these antibodies. The classes and subclasses of the human monoclonal antibody of the present invention include IgG such as IgG1, IgG2, IgG3, and IgG4, IgA such as IGA1 and IGA2, IgD, IgE, and IgM.

The human monoclonal antibody of the present invention typically comprises heavy chain CDR1, heavy chain CDR2, heavy chain CDR3, light chain CDR1, light chain CDR2, and light chain CDR3, and a framework region (FR) is further linked to the amino (N) terminus and the carboxyl (C) terminus of each region of these CDR1 to CDR3.

Among the above-mentioned FRs, examples of a heavy chain FR include heavy chain FR1 linked to the N terminus of heavy chain CDR1, heavy chain FR2 linked between the C terminus of heavy chain CDR1 and the N terminus of heavy chain CDR2, heavy chain FR3 linked between the C terminus of heavy chain CDR2 and the N terminus of heavy chain CDR3, and heavy chain FR4 linked to the C terminus of heavy chain CDR3. Further, among the above-mentioned FRs, examples of a light chain FR include light chain FR1 linked to the N terminus of the light chain CDR1, light chain FR2 linked between the C terminus of light chain CDR1 and the N terminus of light chain CDR2, light chain FR3 linked between the C terminus of light chain CDR2 and the N terminus of light chain CDR3, and light chain FR4 linked to the C terminus of light chain CDR3.

Specific examples of the above-mentioned heavy chain FR1 include (HF1) a polypeptide consisting of amino acid residues 1 to 30 of an amino acid sequence shown in SEQ ID No: 7 and (HF1') a polypeptide consisting of an amino acid sequence having at least 80% or more sequence identity to this polypeptide; specific examples of the above-mentioned heavy chain FR2 include (HF2) a polypeptide consisting of amino acid residues 36 to 49 of the amino acid sequence shown in SEQ ID No: 7 and (HF2') a polypeptide consisting of an amino acid sequence having at least 80% or more sequence identity to this polypeptide; specific examples of the above-mentioned heavy chain FR3 include (HF3) a polypeptide consisting of amino acid residues 67 to 98 of the amino acid sequence shown in SEQ ID No: 7, a polypeptide consisting of amino acid residues 67 to 98 of an amino acid sequence shown in SEQ ID No: 11, and (HF3') a polypeptide consisting of an amino acid sequence having at least 80% or more sequence identity to either of these polypeptides; and specific examples of the above-mentioned heavy chain FR4 include (HF4) a polypeptide consisting of amino acid residues 105 to 115 of the amino acid sequence shown in SEQ ID No: 7 and (HF4') a polypeptide consisting of an amino acid sequence having at least 80% or more sequence identity to this polypeptide.

Specific examples of the above-mentioned light chain FR1 include (LF1) a polypeptide consisting of amino acid residues 1 to 23 of an amino acid sequence shown in SEQ ID No: 8 and (LF1') a polypeptide consisting of an amino acid sequence having at least 80% or more sequence identity to this polypeptide; specific examples of the above-mentioned light chain FR2 include (LF2) a polypeptide consisting of amino acid residues 35 to 49 of the amino acid sequence shown in SEQ ID No: 8 and (LF2') a polypeptide consisting of an amino acid sequence having at least 80% or more sequence identity to this polypeptide; specific examples of the above-mentioned light chain FR3 include (LF3) a polypeptide consisting of amino acid residues 57 to 88 of the amino acid sequence shown in SEQ ID No: 8 and (LF3') a polypeptide consisting of an amino acid sequence having at least 80% or more sequence identity to this polypeptide; and specific examples of the above-mentioned light chain FR4 include (LF4) a polypeptide consisting of amino acid residues 98 to 107 of the amino acid sequence shown in SEQ ID No: 8 and (LF4') a polypeptide consisting of an amino acid sequence having at least 80% or more sequence identity to this polypeptide.

The human monoclonal antibody of the present invention is a human antibody. Examples of the "human antibody" include a human chimeric antibody, a humanized antibody, and a complete human antibody, and preferred examples thereof are a humanized antibody and a complete human antibody.

As used herein, the "human chimeric antibody" has the variable region of an antibody derived from a non-human animal (for example, a non-human mammal such as a chicken, a mouse, a rat, or a bovine) and the constant region of a human-derived antibody linked to each other. The human chimeric antibody can be obtained by, for example, immunizing a non-human animal (preferably a non-human mammal) with an antigen, excising an antibody variable region that binds to the antigen from the gene of the mouse monoclonal antibody, binding it to the gene of the constant region of an antibody derived from the human bone marrow, and incorporating the gene into an expression vector, so that the expression vector is introduced into a host to produce the human chimeric antibody (see, for example, Japanese unexamined Patent Application Publication No. 8-280387; U.S. Pat. Nos. 4,816,397; 4,816,567; and 5,807,715).

Examples of a human constant region of a human chimeric antibody include Cγ1, Cγ2, Cγ3, Cγ4, Cμ, Cδ, Cα1, Cα2, and Cε in the heavy chain and Cκ and Cλ in the light chain. The amino acid sequences of these constant regions and the nucleotide sequences encoding them are known. Further, to improve the stability of an antibody itself or the stability of antibody production, one or more amino acids in the constant region derived from a human antibody can be substituted, deleted, added, and/or inserted.

As used herein, the "humanized antibody" is an antibody obtained by transplanting the gene sequence of the antigen-binding site (a CDR) of an antibody (that is, CDR grafting) derived from a non-human animal (for example, a non-human mammal such as a chicken, a mouse, a rat, or a bovine) into an antibody gene derived from a human, and the methods for preparing it, such as overlap extension PCR, are known (see, for example, European Patent Application No. 239400, European Patent Application No. 125023, International Publication No. WO 90/07861, and International Publication No. WO 96/02576). The variable region of an antibody is usually composed of three CDRs sandwiched by four framework regions (FRs). A CDR is a region that substantially determines the binding specificity of an antibody. While the amino acid sequence of a CDR is rich in diversity, amino acid sequences constituting an FR often show high homology among antibodies having different binding specificity. Thus, it is generally said that the binding specificity of an antibody can be transplanted to other antibodies by transplanting a CDR. Further, in transplantation of a non-human-derived CDR to a human FR, a human FR with high homology to the non-human animal-derived FR is selected from viewpoints of maintaining the function of the CDR. In other words, amino acids in a CDR not only recognize an antigen, but also coordinate with amino acids of an FR in the vicinity of the CDR, and are involved in maintenance of the loop structure of the CDR. Therefore, a human FR consisting of amino acid sequences with high homology to the amino acid sequences of an FR adjacent to a CDR to be transplanted is preferably used.

A known human FR with high homology to a non-human animal-derived FR can be searched by using, for example, a search system which is available on the Internet and specialized in antibodies (<http://www.bioinf.org.uk/abysis/>). A mutation can be introduced into the sequence of a non-human-derived antibody other than CDR so that it is consistent with the sequence of a thus-obtained human FR. Alternatively, when a gene (cDNA) encoding the amino acid sequence of a human FR obtained by search is available, a non-human-derived CDR may be introduced into the sequence. Introduction of a mutation and the like can be performed by using techniques known to the field, such as nucleic acid synthesis and site specific mutation induction.

By qualitatively or quantitatively measuring and assessing the affinity of a humanized antibody prepared in this manner for an antigen, an FR of a human-derived antibody in which the FR is linked via a CDR, and the CDR forms a favorable antigen-binding site can be suitably selected. Further, as necessary, an amino acid residue in the FR can also be substituted in accordance with the method described in "Cancer Res., 1993, 53, 851-856" or the like, so that a CDR of a humanized antibody forms an appropriate antigen-binding site. Further, a variant FR sequence having an intended property can be selected by measuring and assessing the antigen affinity of a variant antibody in which an amino acid has been substituted.

As used herein, the term "complete human antibody" means an antibody in which all sequences in the antibody are human-derived sequences. A complete human antibody can be prepared, for example, in a transgenic mouse which has been engineered so as to express the gene of an antibody having human heavy and light chains. A transgenic mouse producing a human antibody can be prepared in accordance with, for example, the methods described in International Publication No. WO 02/43478, U.S. Pat. No. 6,657,103 (Abgenix), and the like. Further, a hybridoma cell line fused with a B cell derived from a transgenic mouse producing an intended antibody can be prepared in accordance with, for example, the methods described in U.S. Pat. Nos. 5,569,825, 5,625,126, 5,633,425, 5,661,016, 5,545,806, "Jakobovits, Adv. Drug Del. Rev. 31:33-42 (1998)," and "Green, et al, J. Exp. Med. 188:483-95 (1998)."

As described above, the human monoclonal antibody of the present invention also includes one portion (a partial fragment) of an antibody which is a functional fragment specifically recognizing HMGB1 protein, in addition to an antibody consisting of a whole antibody. Examples of such a functional fragment include Fab, Fab', $F(ab')_2$, a variable region fragment (Fv), a disulfide-bond Fv, a single-chain Fv (scFv), $sc(Fv)_2$, a diabody, a polyspecific antibody, and polymers thereof.

The term "Fab" used herein means a monovalent antigen-binding fragment of an immunoglobulin consisting of one light chain and a portion of a heavy chain. A "Fab" can be obtained by papain digestion of an antibody or a genetic recombination method. The term "Fab'" is made different from Fab by adding a small number of residues to the carboxyl terminus of the heavy chain CH1 domain, including one or more cysteines in the hinge region of an antibody. The term "F(ab')$_2$" means a bivalent antigen-binding fragment of an immunoglobulin consisting of portions of two light chains and two heavy chains.

A "variable region fragment (Fv)" is the smallest antibody fragment that has a complete antigen recognizing and binding site. The Fv is a dimer in which a heavy chain variable region and a light chain variable region are strongly linked to each other by a noncovalent bond. The "single-chain Fv (scFv)" comprises a heavy chain variable region and a light chain variable region of an antibody, and these regions exist in a single polypeptide chain. The "sc(Fv)$_2$" is obtained as a single chain by linking two heavy chain variable regions and two light chain variable regions with linkers or the like. The "diabody" is a small antibody fragment having two antigen-binding sites, and this fragment comprises a heavy chain variable region bound to a light chain variable region in the same polypeptide chain, and each region is paired with a complementary region in another chain. The "polyspecific antibody" is a monoclonal antibody having binding specificity to at least two different antigens. For example, a polyspecific antibody can be prepared by simultaneously expressing two pairs of an immunoglobulin heavy chain and a light chain in which two heavy chains have different specificity.

The H chain CDR1 to CDR3 and the L chain CDR1 to CDR3 in the human monoclonal antibody of the present invention include modified CDRs in which one or more amino acids have been substituted, deleted, added, and/or inserted in the amino acid sequences shown in SEQ ID Nos: 1 to 6 without reducing a desirable activity (that is, affinity for HMGB1). The human monoclonal antibody of the present invention comprising the modified CDRs can be prepared by, for example, introducing a mutation into a DNA encoding the antibody chain of the human monoclonal antibody #129 or synthesizing a peptide. Modification of amino acids in regions other than CDRs in an antibody (for example, an FR, a constant region) is considered to have a relatively small effect on the affinity for an antigen. Currently, techniques for screening for an antibody with antigen affinity that has been enhanced by modifying an amino acid of a CDR are known (see, for example, "PNAS, 102:8466-8471 (2005)," "Protein Engineering, Design & Selection, 21:485-493 (2008)," International Publication No. WO 2002/051870, "J. Biol. Chem., 280:24880-24887 (2005)," "Protein Engineering, Design & Selection, 21:345-351 (2008)," or "MAbs. March-April; 6(2):437-45 (2014)"). Further, currently, an antibody with antigen affinity that has been enhanced by utilizing an integrated computational chemistry system or the like (for example, Molecular Operating Environment (MOE; manufactured by Chemical Computing Group [CCG], Canada)) can be modeled (see, for example, <http://www.rsi.co.jp/kagaku/cs/ccg/products/application/protein.htmL>).

As used herein, the expression "(one or) more amino acids" in "one or more amino acids have been substituted, deleted, added, and/or inserted" means preferably 10 or less amino acids, more preferably five or less amino acids, yet more preferably three or less amino acids (for example, two or less amino acids, one amino acid). A preferred example of the substitution, deletion, addition, and insertion of amino acids is conservative substitution. The "conservative substitution" means substitution with other amino acid residues having a chemically similar side chain. Groups of amino acid residues having a chemically similar amino acid side chain are well known in this technical field. For example, acidic amino acids (aspartic acid and glutamic acid), basic amino acids (lysine, arginine, and histidine), and neutral amino acids can be classified into amino acids having a hydrocarbon chain (glycine, alanine, valine, leucine, isoleucine, and proline), amino acids having a hydroxy group (serine and threonine), amino acids containing sulfur (cysteine and methionine), amino acids having an amide group (asparagine and glutamine), an amino acid having an imino group (proline), and amino acids having an aromatic group (phenylalanine, tyrosine, and tryptophan).

As used herein, the expression "at least 80% or more sequence identity" to a predetermined amino acid sequence means preferably at least 85% or more sequence identity, more preferably at least 90% or more sequence identity, yet more preferably at least 95% or more (for example, at least 96% or more, at least 97% or more, at least 98% or more, at least 99% or more, 100%). Homology of amino acid sequences is determined by using a BLASTP (amino acid level) program (see, for example, "J. Mol. Biol., 215:403-410, 1990"). The program is based on a BLAST algorithm (see, for example, "Proc. Natl. Acad. Sci. USA, 87:2264-2268, 1990" and "Proc. Natl. Acad. Sci. USA, 90:5873-5877, 1993"). When amino acid sequences are analyzed using a BLASTP, parameters are set at, for example, a score of 50 and a word length of 3. Further, when amino acid sequences are analyzed using a gapped BLAST program, the analysis can be performed in accordance with the method described in "Nucleic Acids Res. 25:3389-3402, 1997." When a BLAST and a gapped BLAST program are used, default parameters for each program are used. Specific techniques of these analysis methods are known.

The human monoclonal antibody of the present invention also includes human monoclonal antibodies obtained by modifying a process following translation of an antibody, for example, changing the number or position of glycosylation sites. Such modified human monoclonal antibodies can improve the antibody-dependent cellular cytotoxicity (ADCC) activity of an antibody. The glycosylation of an antibody is typically a N-linked or O-linked glycosylation. Glycosylation of an antibody is largely dependent on a host cell used to express the antibody. The glycosylation pattern can be modified by a known method such as introduction or deletion of a specific enzyme involved in sugar production (Japanese unexamined Patent Application Publication No. 2008-113663, U.S. Pat. Nos. 5,047,335, 5,510,261, 5,278,299, International Publication No. WO 99/54342). Further, the human monoclonal antibody of the present invention may be a human monoclonal antibody with deamidation inhibited by substituting a deamidated amino acid or an amino acid adjacent to the deamidated amino acid with another amino acid for the purpose of increasing antibody stability, or a human monoclonal antibody with antibody stability enhanced by substituting glutamic acid with another amino acid.

The human monoclonal antibody of the present invention can be prepared by a known hybridoma method or a known DNA recombination method. Representative examples of the hybridoma method include the method of Kohler and Milstein (see "Nature, 256:495 (1975)"). Examples of the antibody-producing cell used in the cell fusion process in this method include a spleen cell, a lymph node cell, and a peripheral white blood cell of an animal (for example, a mammal such as a mouse, a rat, a hamster, a rabbit, a monkey, or a goat) immunized with an antigen (for example, HMGB1 protein, a partial peptide thereof, a protein obtained by fusing these proteins with Fc protein or the like, a cell expressing these proteins). An antibody-producing cell obtained by allowing an antigen to act on the above-mentioned cell or a lymphocyte isolated beforehand from an unimmunized animal in a medium can also be used. As a myeloma cell, various known cell lines can be used. An antibody-producing cell and a myeloma cell may be derived from different animal species as long as they can be fused, but are preferably derived from an identical animal species as a source. A hybridoma is produced by cell fusion of, for example, a spleen cell obtained from a mouse immunized with an antigen and a mouse myeloma cell, and a hybridoma producing a monoclonal antibody specific to HMGB1 protein can be obtained by subsequent screening. A human monoclonal antibody that specifically binds to HMGB1 protein can be obtained by culturing a hybridoma or from the ascites of a mammal to which a hybridoma has been administered.

The DNA recombination method is a technique in which an antibody gene encoding the human monoclonal antibody of the present invention is cloned from a hybridoma, a B cell, or the like and incorporated into a suitable vector, and this vector is introduced into a host cell (for example, a mammal cell line such as HEK cell, *Escherichia coli*, a yeast cell, an insect cell, a plant cell) to produce the human monoclonal antibody of the present invention as a recombinant antibody (see, for example, "Eur. J. Biochem. 192: 767-775 (1990)"). When an antibody gene encoding the human monoclonal antibody of the present invention is expressed, a host cell may be transformed by incorporating antibody genes encoding a heavy chain and a light chain into separate expression vectors or by incorporating the antibody genes encoding a heavy chain and a light chain into a single expression vector (see International Publication No. WO 94/11523). The human monoclonal antibody of the present invention can be obtained in a substantially pure and uniform form by culturing the above-mentioned host cell and isolating the antibody out of the host cell or a culture broth and purifying it. Isolation and purification of an antibody can be performed by using a method usually used in purification of a polypeptide. By preparing a transgenic animal (for example, a bovine, a goat, a sheep, a swine) into which an antibody gene has been incorporated by using a technique to prepare a transgenic animal, a large amount of a human monoclonal antibody derived from the human monoclonal antibody of the present invention gene can be obtained from milk of the transgenic animal.

Examples of the additive as used herein include pharmaceutically acceptable formulation ingredients such as a carrier, a binder, a stabilizer, an excipient, a diluent, a pH buffer, an isotonic agent, a dissolving aid, and a nutrient. Examples of the pharmaceutically acceptable carrier include mannitol, lactose, sucrose, and human albumin when the agent for preventing or treating of the present invention is a powder; and physiological saline, water for injection, a phosphate buffer solution, and aluminum hydroxide when the agent for preventing or treating of the present invention is a liquid.

A subject for administration of the agent for preventing or treating of the present invention is sufficient as long as the subject (human) requires prevention or treatment of frontotemporal lobar degeneration, and examples thereof include a subject diagnosed as having a high risk of developing frontotemporal lobar degeneration and a patient with frontotemporal lobar degeneration.

Examples of a method for administering the agent for preventing or treating of the present invention include administration by injection (for example, subcutaneous administration, intramuscular administration, intravenous administration, intraarterial administration), administration through an oral cavity mucous membrane, intrarectal administration, local administration into the brain (intracerebroventricular administration), percutaneous administration, and oral administration, and a preferred example is intravenous administration. The dose of the human monoclonal antibody of the present invention in the agent for preventing or treating of the present invention can vary depending on the age, body weight, sex, health condition, and severity of progression of symptoms of a subject for administration, but the dose for adults is usually 0.1 to 1000 mg, preferably 1 to 100 mg per kg of body weight daily. The agent for preventing or treating of the present invention may be used in combination with a known medicine used in the prevention or treatment of frontotemporal lobar degeneration.

The present invention will be specifically described using an example below, but the technical scope of the present invention is not limited to this example. Of note, this example was conducted strictly in compliance with the recommendations in the guidelines on management and use of laboratory animals of the Japanese government and the National Institute of Health Sciences. Further, all experiments were approved by the gene recombination experiment committee, the ethics committee, and the animal experiment committee of the Tokyo Medical and Dental University.

EXAMPLES

1. Materials and Methods

[Anti-Human HMGB1 Antibody]

In this example, a human monoclonal antibody (humanized IgG antibody) #129 prepared in the examples in an international patent application (PCT-JP2019-36926 [International Publication No. WO 2020/059847]) was used as an anti-human HMGB1 antibody. The amino acid sequences of the H chain and the L chain of the human monoclonal antibody #129 are shown in Tables 1 and 2. Of note, when the human monoclonal antibody #129 was subcutaneously administered to a mouse, and the antibody concentrations in the brain and the serum were measured by the ELISA method. The results demonstrated that 2% to 8% of the administered human monoclonal antibody #129 had passed the blood brain barrier (BBB) and had been transferred into the brain.

TABLE 1

| Amino acid sequence of H chain of human monoclonal antibody #129 (SEQ ID No: 9) |
|---|
| EVQLLESGGGLVQPGGSLRLSCAASGFTFSSYAMSWVRQAPGKGLEWVSDISGSGGSTYYADSVK |
| GRFTISRDNSKNTLYLQMNSLRAEDTAVYYCARGYGMDVWGQGTMVTVSSASTKGPSVFPLAPSS |

TABLE 1-continued

| Amino acid sequence of H chain of human monoclonal antibody #129 (SEQ ID No: 9) |
|---|
| KSTSGGTAALGCLVKDYFPEPVTVSWNSGALTSGVHTFPAVLQSSGLYSLSSVVTVPSSSLGTQTYI |
| CNVNHKPSNTKVDKKVEPKSCDKTHTCPPCPAPELLGGPSVFLFPPKPKDTLMISRTPEVTCVVVDV |
| SHEDPEVKFNWYVDGVEVHNAKTKPREEQYNSTYRVVSVLTVLHQDWLNGKEYKCKVSNKALPAPI |
| EKTISKAKGQPREPQVYTLPPSREEMTKNQVSLTCLVKGFYPSDIAVEWESNGQPENNYKTTPPVLD |
| SDGSFFLYSKLTVDKSRWQQGNVFSCSVMHEALHNHYTQKSLSLSPGK |

The underlined region in the table represents the H chain V region (SEQ ID No: 7). The three regions surrounded in a square in the table represent the H chain CDR1 (SEQ ID No: 1), the H chain CDR2 (SEQ ID No: 2), and the H chain CDR3 (SEQ ID No: 3) in order from the amino terminus side.

TABLE 2

| Amino acid sequence of L chain of human monoclonal anibody #129 (SEQ ID No: 10) |
|---|
| DIQMTQSPSSLSASVGDRVTITCRASQSVTNYLAWYQQKPGKAPKLLIYGASILETGVPSRFSGSGS |
| GTDFTLTINSLQPEDFATYYCLQHNSTPLTFGQGTKLEIKTVAAPSVFIFPPSDEQLKSGTASVVCLLN |
| NFYPREAKVQWKVDNALQSGNSQESVTEQDSKDSTYSLSSTLTLSKADYEKHKVYACEVTHQGLSS |
| PVTKSFNRGEC |

The underlined region in the table represents the L chain V region (SEQ ID No: 8). The three regions surrounded in a square in the table represent the L chain CDR1 (SEQ ID No: 4), the L chain CDR2 (SEQ ID No: 5), and the L chain CDR3 (SEQ ID No: 6) in order from the amino terminus side.

[Analysis of Antibody Affinity Using Surface Plasmon Resonance (SPR) Method]

Interactions with human HMGB1 protein were analyzed using the human monoclonal antibody #129 of the present invention and a mouse monoclonal antibody 2C8C described in International Publication No. WO 2018/030405 as a comparative control. Specifically, interactions were measured over time with a surface plasmon resonance measuring device ("Biacore T100"; manufactured by GE Healthcare) using a sensor chip on which the human monoclonal antibody #129 of the present invention or the mouse monoclonal antibody 2C8C was immobilized and the human HMGB1 protein as an analyte, and the equilibrium dissociation constant (KD value), which is an indicator of antibody affinity, was calculated (see FIG. 1).

[Preparation of Four Types of FTLD Model Mice]

Among four types of FTLD model mice (VCP$^{T262A}$-KI mice, PGRN$^{R504X}$-KI mice, CHMP2B$^{Q165X}$-KI mice, and TDP-43$^{N267S}$-KI mice) (herein sometimes referred to as "four types of FTLD model mice"), the PGRN$^{R504X}$-KI mouse was prepared in accordance with the method described in "Nat. Commun., 2018 9, 433."

Further, a targeting vector for preparing the VCP$^{T262A}$-KI mouse was constructed. Specifically, a PCR product of a 5.4-kb NotI-XhoI fragment amplified from a Bac clone (ID: RP23-111G9 or RP23-124L1) was subcloned at the PspOMI-XhoI site in pBS-DTA. Similarly, a 2.9-kb BamHI-NotI fragment amplified from the same Bac clone was subcloned in pBS-LNL(−) having a Neo cassette (loxP-Neo-loxP). A 4.5-kb fragment (the 1.6-kb Neo cassette+the 2.9-kb fragment) was excised by treatment with NotI, and a 0.8-kb XhoI-SmaI fragment having a T262A mutation was amplified from the same Bac clone by PCR and treated with XhoI and SmaI. These 0.8-kb and 4.5-kb fragments were subcloned at the XhoI-NotI site in the targeting vector. After the targeting vector was linearized by treatment with NotI, these fragments were electroporated into ES cells having a C57BL/6J background. VCP$^{T262A}$-KI mice were selected from non-transgenic littermates by PCR using a primer set (Primer 1 [5'-ATATGCTCTCACTGTATGGTATTGC-3'; SEQ ID No: 11] and Primer 2 [5'-TCCAGATGAGCT-TAGAAGATTAGAA-3'; SEQ ID No: 12]) to amplify a DNA fragment containing a LoxP sequence.

Further, a targeting vector for preparing a CHMP2B$^{Q165X}$-KI mouse was constructed. Specifically, a PCR product of a 5.7-kb ClaI-SalI fragment amplified from a Bac clone (ID: RP23-13H5 or RP23-273E18) was subcloned at the ClaI-SalI site in pBS-DTA (manufactured by Unitech Inc.). A 3.0-kb SacII-NotI fragment was amplified from the Bac clone and was subcloned in pBS-LNL(+) having a Neo cassette (loxP-Neo-loxP). A 4.6-kb SacII-NotI fragment (1.6-kb Neo cassette+3.0-kb fragment) was subcloned at the SacII-ClaI site in the targeting vector. CHMP2B$^{Q165X}$-KI mice were selected from non-transgenic littermates by PCR using a primer set (Primer 3 [5'-TGGAT-TTTATTTATGTCTGAATGTG-3'; SEQ ID No: 13] and Primer 4 [5'-ATAAGCAACTTCACAAGGCATCTTA-3'; SEQ ID No: 14]) to amplify a DNA fragment containing a LoxP sequence.

Further, a targeting vector for preparing a TDP-43$^{N267S}$-KI mouse was constructed. Specifically, a 5.9-kb ClaI-SalI fragment was amplified from a Bac clone (ID: RP23-364M1 or RP23-331P21) and subcloned at the ClaI-SalI site in pBS-TK (manufactured by Unitech Inc.). A 2.7-kb SacII-NotI fragment was amplified from the Bac clone and subcloned in pA-LNL(+) having a Neo cassette (loxP-Neo-loxP). A 4.3-kb fragment (1.6-kb Neo cassette+2.7-kb fragment) was subcloned at the SacII-ClaI site in the targeting vector. TDP-43$^{N267S}$-KI mice were selected from non-transgenic littermates by PCR using a primer set (Primer 5 [5'-ACAGTTGGGTGTGATAGCAGGTACT-3'; SEQ ID No: 15] and Primer 6 [5'-TCGAGAATTACAG-GAATGTATCATC-3'; SEQ ID No: 16]) to amplify a DNA fragment containing a LoxP sequence.

[Immunohistochemical Staining Method]

The brain was enucleated from four types of FTLD model mice or C57BL/6J mice of various months of age and immobilized in PBS containing 4% paraformaldehyde for 12 hours, and a paraffin-embedded brain tissue section with a thickness of 5 μm was prepared using a microtome (manufactured by Yamato Kohki Industrial Co., Ltd.). The prepared paraffin-embedded brain tissue section was deparaffinized using xylene, immersed in a 0.01 M citric acid buffer solution (pH 6.0) for re-hydration, and then heated at 120° C. for 15 minutes. Then, permeabilization was performed in PBS containing 0.5% triton-X100, and blocking was performed in PBS containing 10% FBS for 60 minutes. Then, antibody reactions were allowed to occur at 4° C. for 12 hours using various primary antibodies to detect 11 types of proteins (pSer46-MARCKS, γH2AX, 53BP1, phosphorylated TDP-43 [Ser409/410][pSer409/410-TDP-43], ubiquitin, p62, KDEL, MAP2, PSD95, VAMP2, and phosphorylated tau [Ser203 (mouse)/Ser214 (human)] [pSer203 -tau]) (see Table 3). Cells were washed three times with PBS, an antibody reaction was allowed to occur at room temperature for one hour using secondary antibodies against various primary antibodies (see Table 3), cells were washed three times with PBS, the cell nuclei were stained in PBS containing 0.2 μg/mL 4',6-diamidino-2-phenylindole (DAPI), and a fluorescence image derived from the above-mentioned 11 types of proteins and a fluorescence image derived from the cell nuclei were captured using a confocal microscope (FV1200IX83; manufactured by Olympus). Then, the number of pSer46-MARCKS-positive cells per region of 143 μm×143 μm was calculated on the basis of the DAPI fluorescence image and the pSer46-MARCKS fluorescence image (see FIGS. 2-1 and 9). Further, a KDEL signaling region in MAP2-positive cells, wherein the MAP2 is a mature neuron marker, was measured on the basis of the DAPI fluorescence image, the KDEL fluorescence image, and the MAP2 fluorescence image (see FIG. 10). Further, the γH2AX signaling region in MAP2-positive cells was measured on the basis of the DAPI fluorescence image, the γH2AX fluorescence image, and the MAP2 fluorescence image (see FIG. 11). Further, the 53BP1 signaling region in MAP2-positive cells was measured on the basis of the DAPI fluorescence image, the 53BP1 fluorescence image, and the MAP2 fluorescence image (see FIG. 12). Further, the pSer409/410-TDP-43 signaling region in a ubiquitin-positive inclusion was measured on the basis of the DAPI fluorescence image, the pSer409/410-TDP-43 fluorescence image, and the ubiquitin fluorescence image (see FIG. 13). Further, the p62 signaling region in an inclusion was measured on the basis of the DAPI fluorescence image and the p62 fluorescence image (see FIG. 14). Further, the proportion of cells with a VAMP2 signal and a PSD95 signal colocalized therein was measured on the basis of the DAPI fluorescence image, the VAMP2 fluorescence image, and the PSD95 fluorescence image (see FIG. 15). Further, the proportion of cells with a pSer203-tau signal and a PSD95 signal colocalized therein was measured on the basis of the DAPI fluorescence image, the pSer203-tau fluorescence image, and the PSD95 fluorescence image (see FIG. 16).

TABLE 3

| Primary antibody | Secondary antibody (antibody against the primary antibody in the left column) |
|---|---|
| Rabbit anti-pSer46-MARCKS antibody (manufactured by GL Biochem; dilution factor, 1:2,000) | Cy3-labeled anti-rabbit IgG (manufactured by Jackson Laboratory; dilution factor, 1:500) |
| Mouse anti-γH2AX antibody (Ser139; #05-636; manufactured by Millipore; dilution factor, 1:200) | Alexa488-labeled anti-mouse IgG (A21202; manufactured by Molecular Probes; dilution factor, 1:1000) |
| Rabbit anti-53BP1 antibody (NB100-304; manufactured by Novus Biologicals; dilution factor, 1:5,000) | Alexa488-labeled anti-rabbit IgG, (A21206; manufactured by Molecular Probes; dilution factor, 1:1000) |
| Rabbit anti-phosphorylated TDP43 (Ser409/410) antibody (TIP-PTD-P02; manufactured by Cosmo Bio; dilution factor, 1:5,000) | Alexa488-labeled anti-rabbit IgG, (A21206; manufactured by Molecular Probes; dilution factor, 1:1000) |
| Mouse anti-ubiquitin antibody (P4D1; manufactured by Cell Signaling Technology; dilution factor, 1:10,000) | Cy3-labeled anti-mouse IgG (715-165-150; manufactured by Jackson Laboratory; dilution factor, 1:500) |
| Mouse anti-p62 antibody (#610497; manufactured by BD Bioscience; dilution factor, 1:200) | Alexa488-labeled anti-mouse IgG (A21202; manufactured by Molecular Probes; dilution factor, 1:1000) |
| Mouse anti-KDEL antibody (ADI-SPA-827; manufactured by Enzo Life Science; dilution factor, 1:200) | Alexa488-labeled anti-mouse IgG (A21202; manufactured by Molecular Probes; dilution factor, 1:1000) |
| Rabbit anti-MAP2 antibody (ab32454; manufactured by Abcam; dilution factor, 1:1,000) | Cy3-labeled anti-rabbit IgG (manufactured by Jackson Laboratory; dilution factor, 1:500) |
| Mouse anti-MAP2 antibody (sc-32791; manufactured by Santa Cruz Biotechnology; dilution factor, 1:50) | Cy3-labeled anti-mouse IgG, (715-165-150; manufactured by Jackson Laboratory; dilution factor, 1:500) |
| Rabbit anti-PSD95 antibody (D74D3; manufactured by Cell Signaling Technology; dilution factor, 1:200) | Alexa488-labeled anti-rabbit IgG, (A21206; manufactured by Molecular Probes; dilution factor, 1:1000) |
| Mouse anti-VAMP2 antibody (GTX634812; manufactured by Gene Tex; dilution factor, 1:200) | Cy3-labeled anti-mouse IgG, (715-165-150; manufactured by Jackson Laboratory; dilution factor, 1:500) |
| Rabbit anti-phosphorylated tau (Ser203/Ser214) antibody (ab170892; manufactured by Abcam; dilution factor, 1:200) | Cy3-labeled anti-rabbit IgG (manufactured by Jackson Laboratory; dilution factor, 1:500) |
| Mouse anti-PSD95 antibody (MA1-045; manufactured by Thermo Fisher Scientific; dilution factor, 1:200) | Alexa488-labeled anti-mouse IgG (A21202; manufactured by Molecular Probes; dilution factor, 1:1000) |

[Nissl's Staining Method]

The paraffin-embedded brain tissue sections subjected to the deparaffinization treatment and the rehydration treatment in the above-described section of [Immunohistochemical staining method] were washed with deionized water and immersed in a cresyl violet solution (a 300-mL solution containing 0.1% cresyl violet and five drops of 10% acetic acid solution) at 37° C. for 15 minutes. Then, the tissue was dehydrated with an ethanol solution and made transparent with xylene, and then an image of a necrotized brain tissue was captured using an electron microscope (H-7100; manufactured by Hitachi High-Tech Corporation) (see FIG. 2-2).

[Administration of Anti-Human HMGB1 Antibody]

At a frequency of once per month during the treatment period shown in Table 4, 6 μg of the human monoclonal antibody #129 or a control human IgG (#12000C; manufactured by Thermo Fisher Scientific) per 30 g of body weight was administered into the caudal vein of four types of FTLD model mice and the background mouse (C57BL/6J) thereof (FIG. 3). The timing of initiating the antibody administration for each FTLD model mouse was the month of age when development of the disease was confirmed by a Morris water maze test.

TABLE 4

| | $VCP^{T262A}$-KI | $PGRN^{R504X}$-KI | $CHMP2B^{Q165X}$-KI | $TDP43^{N267S}$-KI |
|---|---|---|---|---|
| Duration of treatment with antibody | 6 to 10 months of age | 3 to 7 months of age | 1 to 6 months of age | 6 to 10 months of age |
| Duration of Morris water maze test | 1 to 5 days from 10 months of age | 1 to 5 days from 7 months of age | 1 to 5 days from 6 months of age | 1 to 5 days from 10 months of age |
| Duration of Y-maze test | 7 to 10 months of age | 5 to 7 months of age | 4 to 6 months of age | 7 to 10 months of age |
| Date of fear conditioning test | 10 months of age | 7 months of age | 6 months of age | 10 months of age |

[Cognitive Function Tests]

During each study period or on each study day shown in Table 4, three different cognitive function tests (a Morris water maze test, a Y-maze test, and a fear-conditioning test) were performed on the four types of FTLD model mice in accordance with the method described in "Hum. Mol. Genet. 24, 540-558 (2015)" or "Mol. Psychiatry 20, 459-471 (2015) ." Specifically, in the Morris water maze test, mice underwent a Morris water maze test four times (60 seconds) once daily for five days, and the mean time to reach the platform (latency) (the vertical axis in FIG. 3) was measured. Further, a Y-maze consisting of three identical arms whose angles therebetween are equal (manufactured by O'Hara & Co., Ltd.) was used in the Y-maze test. A mouse was placed at the end of one arm and allowed to behave freely in the maze for eight minutes, and the percentage of spontaneous alternation (expressed as "Alternation rate" on the vertical axis in FIGS. 4 to 7) was calculated by dividing the number of entries into a new arm different from the previous arm by the total number of movements from one arm to another arm. In the fear-conditioning test, freezing responses were measured at 24 hours after conditioning (65 dB white noise for 30 seconds+0.4 mA food shock for 2 seconds) without receiving a foot shock in the same chamber (expressed as [total freeze percent] on the vertical axis in FIG. 8).

[Western Blot Method]

The cerebral cortex tissue from four types of FTLD model mice or C57BL/6J mice at various months of age was dissolved in the presence of a dissolution buffer (100 mM Tris-HCl [pH 7.5], 2% SDS) containing a protease inhibitor cocktail (#539134; manufactured by Calbiochem; dilution factor, 1:100) at 4° C. for one hour. After centrifugation (12,000 g×10 minutes), the supernatant was collected, an equal volume of a sample buffer (62.5 mM Tris-HCl [pH 6.8], 2% [w/v] SDS, 2.5% [v/v] 2-mercaptoethanol, 5% [v/v] glycerol, and 0.0025% [w/v] bromophenol blue) was added, then proteins in the sample were equalized using the BCA method (Pierce BCA protein assay kit; manufactured by Thermo Scientific). Then, a protein sample was isolated by SDS-PAGE, then transferred to a polyvinylidene difluoride (PVDF) membrane (Immobilon-P; manufactured by Millipore) by a semi-dry transfer method, and blocked in a TBST solution containing 5% skim milk (10 mM Tris-HCl [pH 8.0], 150 mM NaCl, 0.05% Tween 20). Using various primary antibodies (see Table 5) to detect 13 types of proteins (phosphorylated PKCα [Ser319] [pSer319-PKCα], phosphorylated PKCγ [Thr655] [pThr655-PKCγ], phosphorylated PKCδ [Ser643] [pSer643-PKCδ], phosphorylated PKCε [Ser729] [pSer729-PKCε], phosphorylated tau [Ser203 (mouse)/Ser214 (human)] [pSer203-tau], PSD95, VAMP2, γH2AX, 53BP1, phosphorylated TDP-43 [Ser409/410] [pSer409/410-TDP-43], pSer46-MARCKS, phosphorylated Ku70 [Ser77/Ser78] [pSer77-Ku70], and β-actin), antibody reactions were allowed to occur in a TBST solution containing 0.1% skim milk or a Can Get Signal solution (manufactured by Toyobo Co., Ltd., Osaka, Japan) at 4° C. for 12 hours. The membrane was washed three times with a TBST solution, and antibody reactions were allowed to occur at room temperature for one hour using secondary antibodies against various primary antibodies (see Table 5). Then, the above-mentioned 13 types of proteins were detected using an ECL Prime Western blot detection reagent (RPN2232; manufactured by GE Healthcare) and a luminescence image analyzer (ImageQuant LAS 500; manufactured by GE Healthcare) (see FIG. 17).

TABLE 5

| Primary antibody | Secondary antibody (antibody against the primary antibody in the left column) |
|---|---|
| Rabbit anti-phosphorylated PKCα (Ser319) antibody (AP0560; manufactured by NeoScientific; dilution factor, 1:10,000) | HRP-binding anti-rabbit IgG (NA934; manufactured by GE Healthcare; dilution factor, 1:3,000) |
| Rabbit anti-phosphorylated PKCγ (Thr655) antibody (ab5796; manufactured by Abcam; dilution factor, 1:10,000) | HRP-binding anti-rabbit IgG (NA934; manufactured by GE Healthcare; dilution factor, 1:3,000) |
| Rabbit anti-phosphorylated PKCδ (Ser643) antibody (#9376; manufactured by Cell Signaling Technology; dilution factor, 1:3,000) | HRP-binding anti-rabbit IgG (NA934; manufactured by GE Healthcare; dilution factor, 1:3,000) |
| Rabbit anti-phosphorylated PKCε (Ser729) antibody (ab63387; manufactured by Abcam; dilution factor, 1:3,000) | HRP-binding anti-rabbit IgG (NA934; manufactured by GE Healthcare; dilution factor, 1:3,000) |
| Rabbit anti-phosphorylated tau (Ser203/Ser214), (ab170892; manufactured by Abcam; dilution factor, 1:10,000) | HRP-binding anti-rabbit IgG (NA934; manufactured by GE Healthcare; dilution factor, 1:3000) |
| Rabbit anti-PSD95 antibody (D74D3; manufactured by Cell Signaling Technology; dilution factor, 1:5,000) | HRP-binding anti-rabbit IgG (NA934; manufactured by GE Healthcare; dilution factor, 1:3,000) |
| Mouse anti-VAMP2 antibody (GTX634812; manufactured by GeneTex; dilution factor, 1:5,000) | HRP-binding anti-mouse IgG (NA931; manufactured by GE Healthcare; dilution factor, 1:3,000) |
| Mouse anti-γH2AX antibody (Ser139; #05-636; manufactured by Millipore; dilution factor, 1:2,000) | HRP-binding anti-mouse IgG (NA931; manufactured by GE Healthcare; dilution factor, 1:3,000) |

TABLE 5-continued

| Primary antibody | Secondary antibody (antibody against the primary antibody in the left column) |
|---|---|
| Rabbit anti-53BP1 antibody (NB100-304; manufactured by Novus Biologicals; dilution factor, 1:50,000) | HRP-binding anti-rabbit IgG (NA934; manufactured by GE Healthcare; dilution factor, 1:3,000) |
| Rabbit anti-phosphorylated TDP43 (Ser409/410) antibody (TIP-PTD-P02; manufactured by Cosmo Bio; dilution factor, 1:6,000) | HRP-binding anti-rabbit IgG (NA934; manufactured by GE Healthcare; dilution factor, 1:3,000) |
| Rabbit anti-pSer46-MARCKS (manufactured by GL Biochem; dilution factor, 1:100,000) | HRP-binding anti-rabbit IgG (NA934; manufactured by GE Healthcare; dilution factor, 1:3,000) |
| Rabbit anti-phosphorylated Ku70 (Ser77/Ser78) antibody (ordered from Cosmo Bio; dilution factor, 1:100,000) | HRP-binding anti-rabbit IgG (NA934; manufactured by GE Healthcare; dilution factor, 1:3,000) |
| Mouse anti-β-actin antibody (manufactured by Santa Cruz Biotechnology; dilution factor, 1:3,000) | HRP-binding anti-mouse IgG (NA931; manufactured by GE Healthcare; dilution factor, 1:3,000) |

2. Results

[Analysis of Antibody Affinity Using Surface Plasmon Resonance (SPR) Method]

While the KD value of the mouse monoclonal antibody 2C8C was $1.95\times10^{-9}$ M, the KD value of the human monoclonal antibody #129 of the present invention was $3.79\times10^{-11}$ M. Given that the KD values of common antibody drugs, as well as the KD value of the mouse monoclonal antibody 2C8C, are within the range of $10^{-9}$ M to $10^{-10}$ M, the human monoclonal antibody #129 of the present invention is shown to be an antibody with very high affinity for human HMGB1.

[Immunohistochemical Staining Method]

pSer46-MARCKS occurs from an early stage before onset of Alzheimer's disease, and HMGB1 leaking out of a cell owing to necrosis of a neuron induces phosphorylation of MARCKS, inducing degeneration of a neurite (see "SCIENTIFIC REPORT, 2016 Aug. 25; 6:31895"). Accordingly, whether phosphorylation of MARCKS and necrosis of neurons also occurred at an early stage of development of FTLD was analyzed using four types of FTLD model mice one to 12 months of age.

Figure 1A:
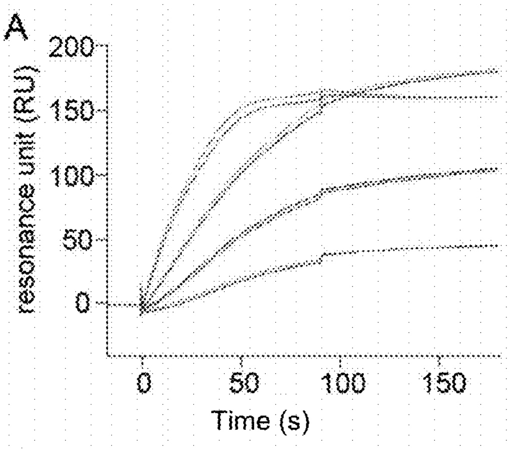
FIG. 1 shows the results of a surface plasmon resonance (SPR) analysis of interactions between two types of anti-human HMGB1 antibodies (the human monoclonal antibody #129 of the present invention [FIG. 1A] and a mouse monoclonal antibody 2C8C [FIG. 1B]) and the human HMGB1 protein.
Figure 1B:
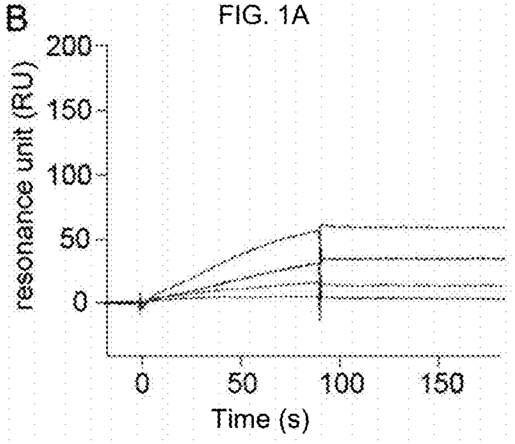
Figures 1A, 2:
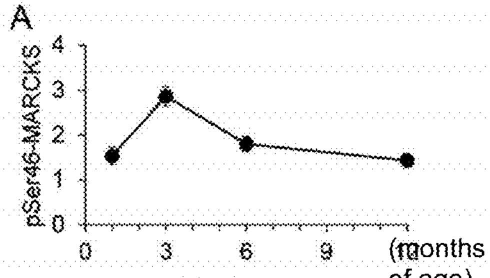
Figures 1B, 2:
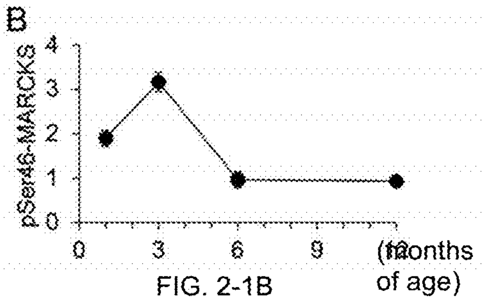
Figures 1C, 2:
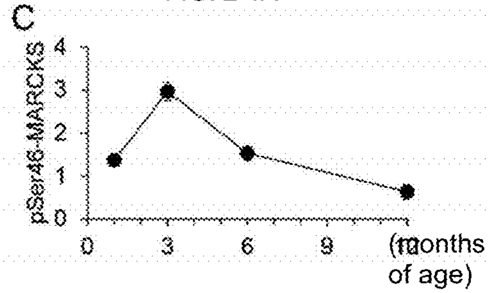
Figures 1D, 2:
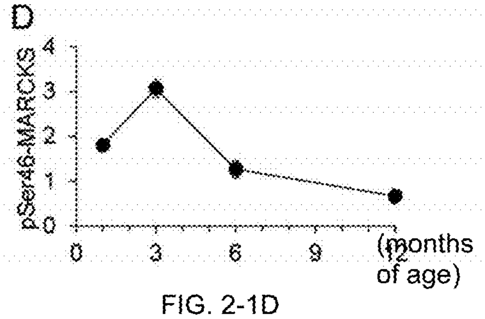
Figures 2, 2A:
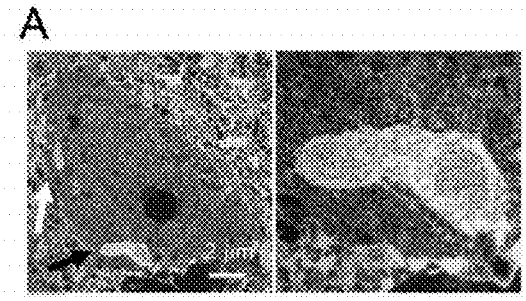
Figures 2, 2B:
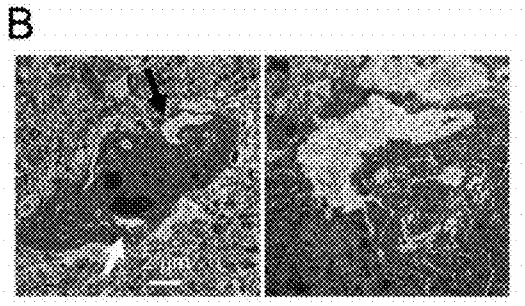

In the results, cells showing a high level of a pSer46-MARCKS-derived signal and an attenuated genomic DNA-derived DAPI signal were observed in cerebral cortex in the four types of FTLD model mice ($VCP^{T262A}$-KI mice, $PGRN^{R504X}$-KI mice, $CHMP2B^{Q165X}$-KI mice, and $TDP\text{-}43^{N267S}$-KI mice) at one month, three months, six months, and 12 months of age (see FIG. 2-1). Further, expansion of the endoplasmic reticulum (ER), which is characteristic to necrosis, was observed in the cerebral cortex in two types of FTLD model mice ($VCP^{T262A}$-KI mice and $PGRN^{R504X}$-KI mice) at one month of age (see FIG. 2-2).

These results indicate that necrosis occurs from an early stage of development of FTLD.

[Treatment Effect of Human Monoclonal Antibody #129 on Symptoms of FTLD Model Mice: Cognitive Function Tests]

Subsequently, whether FTLD symptoms improved when the human monoclonal antibody #129 of the present invention was administered to four types of FTLD model mice was analyzed using three types of cognitive function tests (a Morris water maze test, a Y-maze test, and a fear-conditioning test). First, the Morris water maze test demonstrated that the time to reach the platform was prolonged as the four types of FTLD model mice aged by month ("KI n.t." in FIG. 3), as compared with C57BL/6J mice ("B6 n.t." in FIG. 3), which are normal mice (see FIG. 3). In contrast, it was shown that, when the human monoclonal antibody #129 of the present invention was administered to the four types of FTLD model mice ("KI Ab" in FIG. 3), the prolongation of time to reach the platform was significantly suppressed (the time was shortened) in all the FTLD model mice from an early stage of development of FTLD regardless of types of FTLD mutant genes to the same extent as in the C57BL/6J mice, whereas, when a control human IgG was administered to the four types of FTLD model mice ("KI IgG" in FIG. 3), no change was observed in the prolongation of time to reach the platform (see FIG. 3).

These results indicate that the human monoclonal antibody #129 of the present invention has an effect of preventing and improving the decreased cognitive function caused by FTLD. Effects similar to these results were also confirmed when a Y-maze test (see FIGS. 4 to 7) and a fear-conditioning test (see FIG. 8) were performed.

[Treatment Effect of Human Monoclonal Antibody #129 on Symptoms in FTLD Model Mice: Immunohistochemical Staining Method]

Subsequently, the effect of the human monoclonal antibody #129 of the present invention of improving cognitive function in FTLD was analyzed using an immunohistochemical staining method. First, in the four types of FTLD model mice ("KI n.t." in FIG. 3), as compared with the C57BL/6J mice ("B6 n.t." in FIG. 3), which are normal mice, the proportion of necrosis marker (pSer46-MARCKS)-positive cells in the cerebral cortex increased (see FIG. 9), and the ER marker (KDEL)-derived signaling region expanded (see FIG. 10). In contrast, it was shown that, when the human monoclonal antibody #129 of the present invention was administered to the four types of FTLD model mice ("KI Ab" in FIGS. 9 and 10), the increases in the proportion of pSer46-MARCKS-positive cells and the expansion of the KDEL-derived signaling region were significantly suppressed to the same extent as in the C57BL/6J mice, whereas, when a control human IgG was administered to the four types of FTLD model mice ("KI IgG" in FIGS. 9 and 10), no changes were observed in the increase in the proportion of the pSer46-MARCKS-positive cells or the expansion of the KDEL-derived signaling region (see FIGS. 9 and 10).

These results indicate that the human monoclonal antibody #129 of the present invention has an effect of preventing and improving necrosis and ER expansion in the cerebral cortex caused by FTLD.

Further, in the four types of FTLD model mice, as compared with the C57BL/6J mice, the DNA damage marker (γH2AX and 53BP1)-derived signaling region in the cerebral cortex expanded. However, it was shown that, when the human monoclonal antibody #129 of the present invention was administered, the expansion of the γH2AX and 53BP1-derived signaling region was significantly suppressed to the same extent as in the C57BL/6J mice (see FIGS. 11 and 12).

These results indicate that the human monoclonal antibody #129 of the present invention has an effect of preventing and improving DNA damage in the cerebral cortex caused by FTLD.

Further, in the four types of FTLD model mice, as compared with the C57BL/6J mice, the protein agglutination marker (pSer409/410-TDP-43 and p62)-derived signaling region expanded in the cerebral cortex. However, it was shown that, when the human monoclonal antibody #129 of the present invention was administered, the expansion of the pSer409/410-TDP-43 and p62-derived signaling region was significantly suppressed (see FIGS. 13 and 14).

These results indicate that the human monoclonal antibody #129 of the present invention has an effect of preventing and improving protein agglutination in the cerebral cortex caused by FTLD.

Further, the present inventors investigated synapse damage by analysis of a phosphorylated proteome using colocalization of VAMP2 and PSD95 and colocalization of pSer203-tau and PSD95 as indicators. Thus, the results of the analysis of synapse damage using these colocalizations as indicators showed that colocalization of VAMP2 and PSD95 in the cerebral cortex had decreased in the four types of FTLD model mice, as compared with the C57BL/6J mice, but the decrease was significantly suppressed when the human monoclonal antibody #129 of the present invention was administered (see FIG. 15). Further, colocalization of pSer203-tau and PSD95 increased in the cerebral cortex of the four types of FTLD model mice as compared with the C57BL/6J mice. However, it was shown that, when the human monoclonal antibody #129 of the present invention was administered, the increase was significantly suppressed (see FIG. 16).

These results indicate that the human monoclonal antibody #129 of the present invention has an effect of preventing and improving synapse damage in the cerebral cortex caused by FTLD.

[Treatment Effect of Human Monoclonal Antibody #129 on Symptoms of FTLD Model Mice: Western Blot Method]

To support the results of the analysis using the immunohistochemical staining method, an analysis using Western blot method was performed. First, when the phosphorylation levels of four types of proteins associated with an AD-FTLD core signal (pSer319-PKCα, pThr655-PKCγ, pSer643-PKCδ, and pSer729-PKCε) were analyzed, the results showed that the phosphorylation levels of two types of proteins (pSer319-PKCα and pSer643-PKCδ) predicted by a dynamic network analysis with a strict threshold for core node selection (centricity>2SD) increased in the four types of FTLD model mice as compared with the C57BL/6J mice. However, when the human monoclonal antibody #129 of the present invention was administered to the four types of FTLD model mice, the increases in the pSer319-PKCα and pSer643-PKCδ levels were suppressed (see Lanes (1) and (3) in FIG. 17). In contrast, no difference was observed in the phosphorylation levels of two types of proteins (pThr655-PKCγ and pSer729-PKCε) predicted by a dynamic network analysis under a relatively loose condition for a core node selection (centricity>0) between the above-mentioned four types of FTLD model mice and the C57BL/6J mice (see Lanes (2) and (4) in FIG. 17).

Further, the phosphorylation level of the synapse instability-associated protein (pSer203-tau) increased in the four types of FTLD model mice as compared with the C57BL/6J mice. However, it was shown that, when the human monoclonal antibody #129 of the present invention was administered to the four types of FTLD model mice, the increase in the pSer203-tau level was suppressed (see Lane (5) in FIG. 17). Further, the expression levels of synapse-associated proteins (PSD95 and VAMP2) decreased in the four types of FTLD model mice as compared with the C57BL/6J mice. However, it was shown that, when the human monoclonal antibody #129 of the present invention was administered to the four types of FTLD model mice, the decreases in the expression levels of PSD95 and VAMP2 were suppressed (see Lanes (6) and (7) in FIG. 17).

Further, the expression levels of DNA damage-associated proteins (γH2AX and 53BP1) increased in the four types of FTLD model mice as compared with the C57BL/6J mice. However, it was shown that, when the human monoclonal antibody #129 of the present invention was administered to the four types of FTLD model mice, the increases in the expression levels of γH2AX and 53BP1 were suppressed (see Lanes (8) and (9) in FIG. 17).

Further, the phosphorylation level of the cell death-associated protein (pSer46-MARCKS) increased in the four types of FTLD model mice as compared with the C57BL/6J mice. However, it was shown that, when the human monoclonal antibody #129 of the present invention was administered to the four types of FTLD model mice, the increase in the pSer46-MARCKS level was suppressed (see Lane (10) in FIG. 17).

Further, the phosphorylation level of the DNA repair-associated protein (pSer77-Ku70) increased in the four types of FTLD model mice as compared with the C57BL/6J mice. However, it was shown that, when the human monoclonal antibody #129 of the present invention was administered to the four types of FTLD model mice, the increase in the pSer77-Ku70 level was suppressed (see Lane (11) in FIG. 17).

Further, the protein agglutination marker level (pSer409/410-TDP-43) increased in the four types of FTLD model mice as compared with the C57BL/6J mice. However, it was shown that, when the human monoclonal antibody #129 of the present invention was administered to the four types of FTLD model mice, the increase in the pSer409/410-TDP-43 level was suppressed (see Lane (12) in FIG. 17).

The above results indicate that the human monoclonal antibody #129 of the present invention has an effect of preventing and improving secondary neuron damage and neurite damage induced by extracellular HMGB1 released from necrotized neurons by FTLD.

[Adverse Reactions of the Human Monoclonal Antibody #129 of the Present Invention]

Further, adverse reactions of the human monoclonal antibody #129 of the present invention were investigated. After the cognitive function tests shown in FIGS. 3 to 8, the human monoclonal antibody #129 of the present invention was administered to the four types of FTLD model mice and the C57BL/6J mice, then the lung, liver, kidney, intestine, spleen, skeletal muscle, heart, and skin were removed therefrom by incision, and a pathological examination was performed.

The results showed no abnormal findings (for example, obvious inflammation, cell death, tumor) due to administration of the human monoclonal antibody #129 of the present invention in any tissue. The results indicate that the human monoclonal antibody #129 of the present invention can prevent and improve symptoms in FTLD model mice without causing noticeable adverse reactions.

INDUSTRIAL APPLICABILITY

The present invention contributes to prevention and/or treatment of FTLD.

The invention claimed is:

1. A method for treating frontotemporal lobar degeneration, comprising administering a human monoclonal antibody that specifically binds to human HMGB1 and comprises:

a heavy chain complementarity determining region (CDR) 1 consisting of the amino acid sequence shown in SEQ ID No: 1; a heavy chain CDR2 consisting of the amino acid sequence shown in SEQ ID No: 2; and a heavy chain CDR3 consisting of the amino acid sequence shown in SEQ ID No: 3; and a light chain CDR1 consisting of the amino acid sequence shown in SEQ ID No: 4; a light chain CDR2 consisting of the amino acid sequence shown in SEQ ID No: 5; and a light chain CDR3 consisting of the amino acid sequence shown in SEQ ID No: 6, to a subject in need of treatment of frontotemporal lobar degeneration.

2. The method according to claim 1, wherein the human monoclonal antibody comprises a heavy chain variable region consisting of an amino acid sequence having at least 80% or more sequence identity to the amino acid sequence shown in SEQ ID No: 7, and a light chain variable region consisting of an amino acid sequence having at least 80% or more sequence identity to the amino acid sequence shown in SEQ ID No: 8.

3. The method according to claim 1, wherein the human monoclonal antibody comprises a heavy chain consisting of an amino acid sequence having at least 80% or more sequence identity to the amino acid sequence shown in SEQ ID No: 9, and a light chain consisting of an amino acid sequence having at least 80% or more sequence identity to the amino acid sequence shown in SEQ ID No: 10.

4. The method according to claim 1, wherein the human monoclonal antibody is intravenously administered.

5. The method according to claim 2, wherein the human monoclonal antibody comprises a heavy chain consisting of an amino acid sequence having at least 80% or more sequence identity to the amino acid sequence shown in SEQ ID No: 9, and a light chain consisting of an amino acid sequence having at least 80% or more sequence identity to the amino acid sequence shown in SEQ ID No: 10.

6. The method according to claim 2, wherein the human monoclonal antibody is intravenously administered.

7. The method according to claim 3, wherein the human monoclonal antibody is intravenously administered.

8. The method according to claim 5, wherein the human monoclonal antibody is intravenously administered.

* * * * *

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial
<220> FEATURE:
<223> OTHER INFORMATION: Heavy Chain Complementarity Determination
      Region 1 of human monoclonal antibody #129
<220> FEATURE:
<221> NAME/KEY: MISC_FEATURE
<223> OTHER INFORMATION: Inventor:OKAZAWA, Hitoshi

<400> SEQUENCE: 1

Ser Tyr Ala Met Ser
1               5


<210> SEQ ID NO 2
<211> LENGTH: 17
<212> TYPE: PRT
<213> ORGANISM: Artificial
<220> FEATURE:
<223> OTHER INFORMATION: Heavy Chain Complementarity Determination
      Region 2 of human monoclonal antibody #129

<400> SEQUENCE: 2

Asp Ile Ser Gly Ser Gly Gly Ser Thr Tyr Tyr Ala Asp Ser Val Lys
1               5                   10                  15

Gly


<210> SEQ ID NO 3
<211> LENGTH: 6
<212> TYPE: PRT
<213> ORGANISM: Artificial
<220> FEATURE:
<223> OTHER INFORMATION: Heavy Chain Complementarity Determination
      Region 3 of human monoclonal antibody #129

<400> SEQUENCE: 3

Gly Tyr Gly Met Asp Val
1               5


<210> SEQ ID NO 4
<211> LENGTH: 11
<212> TYPE: PRT
<213> ORGANISM: Artificial
<220> FEATURE:
<223> OTHER INFORMATION: Light Chain Complementarity Determination
      Region 1 of human monoclonal antibody #129

<400> SEQUENCE: 4

Arg Ala Ser Gln Ser Val Thr Asn Tyr Leu Ala
1               5                   10


<210> SEQ ID NO 5
<211> LENGTH: 7
<212> TYPE: PRT
<213> ORGANISM: Artificial
<220> FEATURE:
<223> OTHER INFORMATION: Light Chain Complementarity Determination
      Region 2 of human monoclonal antibody #129

<400> SEQUENCE: 5

Gly Ala Ser Ile Leu Glu Thr
1               5


<210> SEQ ID NO 6
```

```
<211> LENGTH: 9
<212> TYPE: PRT
<213> ORGANISM: Artificial
<220> FEATURE:
<223> OTHER INFORMATION: Light Chain Complementarity Determination
      Region 3 of human monoclonal antibody #129

<400> SEQUENCE: 6

Leu Gln His Asn Ser Thr Pro Leu Thr
1               5


<210> SEQ ID NO 7
<211> LENGTH: 115
<212> TYPE: PRT
<213> ORGANISM: Artificial
<220> FEATURE:
<223> OTHER INFORMATION: Heavy Chain Variable Region of human monoclonal
      antibody #129

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Met Asp Val Trp Gly Gln Gly Thr Met Val Thr
            100                 105                 110

Val Ser Ser
        115


<210> SEQ ID NO 8
<211> LENGTH: 107
<212> TYPE: PRT
<213> ORGANISM: Artificial
<220> FEATURE:
<223> OTHER INFORMATION: Light Chain Variable Region of human monoclonal
      antibody #129

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Thr Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Ile Leu Glu Thr Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln His Asn Ser Thr Pro Leu
                85                  90                  95

Thr Phe Gly Gln Gly Thr Lys Leu Glu Ile Lys
            100                 105
```

<210> SEQ ID NO 9
<211> LENGTH: 445
<212> TYPE: PRT
<213> ORGANISM: Artificial
<220> FEATURE:
<223> OTHER INFORMATION: Heavy Chain of human monoclonal antibody #129

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Met Asp Val Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

-continued

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 10
<211> LENGTH: 213
<212> TYPE: PRT
<213> ORGANISM: Artificial
<220> FEATURE:
<223> OTHER INFORMATION: Light Chain of human monoclonal antibody #129

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Thr Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Ile Leu Glu Thr Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln His Asn Ser Thr Pro Leu
                85                  90                  95

Thr Phe Gly Gln Gly Thr Lys Leu Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 11
<211> LENGTH: 25
<212> TYPE: DNA
<213> ORGANISM: Artificial
<220> FEATURE:
<223> OTHER INFORMATION: primer 1

<400> SEQUENCE: 11

atatgctctc actgtatggt attgc                                           25
```

-continued

<210> SEQ ID NO 12
<211> LENGTH: 25
<212> TYPE: DNA
<213> ORGANISM: Artificial
<220> FEATURE:
<223> OTHER INFORMATION: primer 2

<400> SEQUENCE: 12
tccagatgag cttagaagat tagaa 25

<210> SEQ ID NO 13
<211> LENGTH: 25
<212> TYPE: DNA
<213> ORGANISM: Artificial
<220> FEATURE:
<223> OTHER INFORMATION: primer 3

<400> SEQUENCE: 13
tggattttat ttatgtctga atgtg 25

<210> SEQ ID NO 14
<211> LENGTH: 25
<212> TYPE: DNA
<213> ORGANISM: Artificial
<220> FEATURE:
<223> OTHER INFORMATION: primer 4

<400> SEQUENCE: 14
ataagcaact tcacaaggca tctta 25

<210> SEQ ID NO 15
<211> LENGTH: 25
<212> TYPE: DNA
<213> ORGANISM: Artificial
<220> FEATURE:
<223> OTHER INFORMATION: primer 5

<400> SEQUENCE: 15
acagttgggt gtgatagcag gtact 25

<210> SEQ ID NO 16
<211> LENGTH: 25
<212> TYPE: DNA
<213> ORGANISM: Artificial
<220> FEATURE:
<223> OTHER INFORMATION: primer 6

<400> SEQUENCE: 16
tcgagaatta caggaatgta tcatc 25